United States Patent
Wilmanowicz

(10) Patent No.: US 10,806,765 B2
(45) Date of Patent: Oct. 20, 2020

(54) IMMUNOLOGICALLY ACTIVE PHYTO-MIXTURE AND ITS USE IN THE PREVENTION AND IN A METHOD FOR TREATMENT OF EFFLORESCENCES

(71) Applicant: Renate Wilmanowicz, Düsseldorf (DE)

(72) Inventor: Renate Wilmanowicz, Düsseldorf (DE)

(*) Notice: Subject to any disclaimer, the term of this patent is extended or adjusted under 35 U.S.C. 154(b) by 0 days.

(21) Appl. No.: 16/191,239

(22) Filed: Nov. 14, 2018

(65) Prior Publication Data

US 2019/0183953 A1 Jun. 20, 2019

Related U.S. Application Data

(62) Division of application No. 15/550,600, filed as application No. PCT/EP2016/052836 on Feb. 10, 2016, now abandoned.

(30) Foreign Application Priority Data

Feb. 12, 2015 (DE) .................. 10 2015 102 020

(51) Int. Cl.
| | | |
|---|---|---|
| *A61K 36/28* | (2006.01) | |
| *A61K 36/85* | (2006.01) | |
| *A61K 36/886* | (2006.01) | |
| *A61K 36/32* | (2006.01) | |
| *A61K 36/68* | (2006.01) | |
| *A61K 8/97* | (2017.01) | |

(52) U.S. Cl.
CPC ............ *A61K 36/28* (2013.01); *A61K 8/97* (2013.01); *A61K 36/32* (2013.01); *A61K 36/68* (2013.01); *A61K 36/85* (2013.01); *A61K 36/886* (2013.01)

(58) Field of Classification Search
CPC ..................................................... A61K 36/00
USPC ......................................................... 424/725
See application file for complete search history.

(56) References Cited

U.S. PATENT DOCUMENTS

| | | |
|---|---|---|
| 2008/0166435 A1 | 7/2008 | Pylypchuk |
| 2009/0062216 A1 | 3/2009 | Yang et al. |
| 2018/0036360 A1 | 2/2018 | Wilmanowicz |

FOREIGN PATENT DOCUMENTS

| | | | |
|---|---|---|---|
| CN | 102743651 A | | 10/2012 |
| DE | 102015102020 | | 8/2016 |
| EP | 0 114 709 A1 | | 8/1984 |
| JP | 02002193786 A | * | 7/2002 |
| JP | 2004/352680 | | 12/2004 |
| JP | 2004-359732 | | 12/2004 |
| RU | 2412719 C2 | | 2/2011 |
| WO | WO 2008/029136 A1 | | 3/2008 |
| WO | WO 2016/128471 | | 8/2016 |

OTHER PUBLICATIONS

Camporese et al. (2003) Screening of anti-bacterial activity of medicinal plants from Belize (Central America). Journal of Ethnopharmacology 87:103-107.
Chariandy et al. (1999) Screening of medicinal plants from Trinidad and Tobago for antimicrobial and insecticidal properties. Journal of Ethnopharmacology 64:265-270.
Database WPI, Week 200167, Thomson Scientific. London. GB; AN 2001-5925233, XP002756143 & JP 2001 178390 A (Musashino Meneki Kenkyusho KK) Jul. 3, 2001 (abstract).
De Rodriguez et al. (2006) pp. 325-377, Rai, M [Editor]; Carpinella, MC [Editor]. Naturally Occurring Bioactive Compounds. Publisher: Elsevier Science BV, Sara Burgerhartstraat 25, PO Box 211, 1000 AE Amsterdam, Netherlands. Series: Advances in Phytomedicine.
Elston (2009) Topical Antibiotics in Dermatology: Emerging Patterns of Resistance. Dermatol Clin 27:25-31.
Ferrer et al. (2011) Boletin Latinoamericano y del Caribe de Plantas Medicinales y Aromaticas 10(1):75-82.
Geissberger & Séquin (1991) Constituents of *Bidens pilosa* L.: Do the compounds found so far explain the use of this plant in traditional medicine? Acta Tropica 48:251-261.
Hudson (2012) Applications of the Phytomedicine *Echinacea purpurea* (Purple Coneflower) in Infectious Diseases. Journal of Biomedicine and Biotechnology 2012:1-16.
International Preliminary Report on Patentability corresponding to International Patent Application No. PCT/EP2016/052836 dated May 10, 2017.
International Search Report corresponding to International Patent Application No. PCT/EP2016/052836 dated Jun. 27, 2016.
Mantaring-Chua (1991) Quantitative Microbial Assay, Clinical Testing and Stability Studies of the Crude Leaf Extract of *Bidens pilosa* Linn. Acta Manilana 39:31-37.
NCTC 10442.
Noguera et al. (2004) Anti-inflammatory activity of leaf extract and fractions of *Bursera simaruba* (L.) Sarg (Burseraceae). Int J Ethnopharm 92:129-133.
Office Action (Restriction Requirement) corresponding to U.S. Appl. No. 15/550,600 dated Nov. 24, 2017.

(Continued)

*Primary Examiner* — Michael V Meller
(74) *Attorney, Agent, or Firm* — Jenkins, Wilson, Taylor & Hunt, P.A.

(57) ABSTRACT

The present invention relates to an immunologically active phyto-mixture comprising at least one plant extract selected from the family (a) Asteraceae, (b) Verbenaceae, and/or (c) Burseraceae, preferably at least one plant extract from the genus (a) *Bidens*, (b) *Stachytarpheta*, and/or (c) *Bursera*. Particularly preferred species include (a) *Bidens alba, Bidens pilosa*, (b) *Stachytarpheta jamaicensis, Stachytarpheta cayennensis, Stachytarpheta indica*, and/or (c) *Bursera simaruba, Bursera microphylla, Bursera glabrifolia*. The phyto-mixture optionally comprises (d) at least one further biologically active plant extract, such as *Aloe vera* and/or *Stemodia maritima*. The afore-mentioned phyto-mixture according to the invention exhibits good antimicrobial and anti-inflammatory efficiency and is particularly suitable for prevention and treatment of efflorescences. Therefore, the present invention also relates to a preparation for oral and topical administration for prevention and treatment of efflorescences of the skin and the mucous membrane.

19 Claims, No Drawings

(56) References Cited

OTHER PUBLICATIONS

Office Action corresponding to German Patent Application No. 10 2015 102 020.3 dated Oct. 9, 2015.
Office Action corresponding to U.S. Appl. No. 15/550,600 dated Aug. 15, 2018.
Office Action corresponding to U.S. Appl. No. 15/550,600 dated Mar. 28, 2018.
Okoye et al. (2010) Antinucrobial and antispasn1odic activity of leaf extract and fractions of Stachytarpheta cayennensis. Asian Pacific Journal of Tropical Medicine 2010:189-192.
Rojas et al. (2006) Screening for antimicrobial activity of ten medicinal plants used in Colombian folkloric medicine: A possible alternative in the treatment of non-nosocomial infections. BMC Complementary and Alternative Medicine 6:1-6.
Russell et al. (2011) Stemodin-derived analogues with lipid peroxidation, cyclooxygenase enzymes and human tumour cell proliferation inhibitory activities. Phytochemistry 72:2361-2368.
Schapoval et al. (1998) Antiinflammatory and antinociceptive activities of extracts and isolated compounds from Stachytarpheta cayennensis. Int J Ethnopharm 60:53-59.
US Wildflower, 3 pages, 2018.
Yasunaka et al. (2005) Antibacterial activity of crude extracts from Mexican medicinal plants and purified coumarins and xanthones. Int J Ethnopharm 97:293-299.

\* cited by examiner

IMMUNOLOGICALLY ACTIVE PHYTO-MIXTURE AND ITS USE IN THE PREVENTION AND IN A METHOD FOR TREATMENT OF EFFLORESCENCES

The present invention relates to an immunologically active phyto-mixture comprising at least one plant extract selected from the family (a) Asteraceae, (b) Verbenaceae, and/or (c) Burseraceae, preferably from the genus (a) *Bidens*, (b) *Stachytarpheta*, and/or (c) *Bursera*. Particularly preferred species include (a) *Bidens alba, Bidens pilosa*, (b) *Stachytarpheta jamaicensis, Stachytarpheta cayennensis, Stachytarpheta indica*, and/or (c) *Bursera microphylla, Bursera glabrifolia* and *Bursera simaruba*. The phyto-mixture optionally comprises (d) at least one further biologically active plant extract, such as *Aloe vera* and/or *Stemodia maritima*. The afore-mentioned phyto-mixture according to the invention exhibits good antimicrobial and anti-inflammatory efficiency and is particularly suitable for prevention and treatment of efflorescences. Therefore, the present invention also relates to a preparation for oral and topical administration for prevention and treatment of efflorescences of the skin and the mucous membrane.

In modern medicine, comprehensive synthetically produced pharmaceutical products for prevention or treatment of skin irritations and skin diseases are provided for the patients. These are prescribed by the doctor as authorised medicaments or are available as nonprescription medical products. However, due to synthetic active agents, the pharmaceutic compositions increasingly cause side effects, cause allergic reactions or result in steadily growing resistances in infection germs causing the skin irritations or diseases.

Therefore, there are more and more aspirations for isolating new active agents, continuously having efficiency against resistant germs, causing few or no side effects or allergic reactions in human, and potentially having an improved resorption in human. For this purpose, microorganisms itself or plants may be used as source of new acting agents.

In the case of plant sources, some compound classes, such as, for example flavones, are isolated and processed into pharmaceutic preparations. RU2412719 discloses such flavone extracts for medicaments for treatment of liver diseases. CN102743651 discloses a mixture of 30 different plants in the form of a lotion for treatment of cellulitis.

In the state of the art, miscellaneous plants, in particular from traditional medicine, are tested for their efficiency, their ingredients are identified, the toxicity is analysed, but only less or no efficiency is observed (EP114709A1).

Previously, only few analyses have been performed for plant preparations and no one has both antibacterial and anti-inflammatory efficiency. Consequently, no plant alternative to synthetic active agents, such as, for example antibiotics, or synthetic inflammation inhibitors has previously been detected.

The present invention provides the object of providing new preparations having effective ingredients from natural sources, in particular effective ingredients of plant sources. A further object is to provide a plant product and preparations having antimicrobially, preferably antibacterially, and/or anti-inflammatorily effective ingredients. In this context, various possible combinations of some plant products, such as plant extracts, shall be provided, which may individually be mixed for the user. A further object is the provision of a phyto-mixture for the production of preparations for preventive use or therapeutic use in the treatment of efflorescences. For this purpose, pharmaceutic compositions, care products, nutritional supplements, as well as medical products comprising a phyto-mixture from total extracts of plants shall be provided. Moreover, the present invention provides the object of providing a natural product as alternative to synthetically produced products. The object is to provide a natural product from plant sources, in particular for humans, in which the synthetically produced products known from the state of the art exhibit strongly reduced or no more efficiency and/or increasingly cause side effects. The afore-mentioned plant products and their preparations comprising the phyto-mixture shall be provided for prevention and treatment of efflorescences.

The present invention therefore provides a natural product from plant sources, having both antimicrobial, preferably antibacterial, and anti-inflammatory effect.

Therefore, a subject matter of the present invention is an immunologically active phyto-mixture comprising at least one plant extract selected from (a) the species *Bid. alba, Bid. pilosa, Bid. bipinnata* and *Bid. parviflora*, preferably *Bidens alba* and/or *Bidens pilosa*, from genus *Bidens* of the Asteraceae family, (b) the species *Stachytarpheta jamaicensis, Stachytarpheta indica* and *Stachytarpheta cayennensis* from genus *Stachytarpheta* of the Verbenaceae family, and/or (c) the species *Bursera microphylla, Bursera glabrifolia* and/or *Bursera simaruba* from genus *Bursera* of the Burseraceae family, and optionally, additionally (d) at least one further extract of a biologically active plant, as described below.

In the case where the wording "plant extracts (a), (b), and/or (c)" is used without limitation to a specific species, it shall be understood to mean an abbreviation of the afore-mentioned wording. In the following, the name of the appropriate genus is abbreviated (a) *Bidens* by "*Bid.*", (b) *Stachytarpheta* by "*Sta.*", and (c) *Bursera* by "*Bur.*".

Preferably, the afore-mentioned plant extracts are aqueous or ethanolic extracts (greater than or equal to 70% ethanol, remainder water) The "immunologically active phyto-mixture" according to the invention is briefly, thus synonymously, termed as "phyto-mixture".

Within the meaning of the invention, "immunologically active" means that the phyto-mixture according to the invention, in particular the contained ingredients and compounds, prevents, inhibits or reduces immune reactions of the body. "Immunologically active" comprises preventive effect so that immune reactions of the body are not even being triggered, and therapeutic effect so that the already triggered immune reactions in the body are stopped, downregulated or reduced. Depending on administration time, the beginning immune reaction may be inhibited prior to occurring of symptoms, accompanying with immune reaction, and phenotypic appearances. Endogenous microorganisms, pathogens influencing in/on the body, such as bacteria, viruses, fungi and parasites, or toxic and/or influencing compounds triggering allergic reactions may be trigger of the afore-mentioned immune reactions.

The immune response of the immune system to an organism, in particular microorganisms, or substance, in particular toxins, is termed as immune reactions.

What triggers the afore-mentioned immune reaction depends on constitution of the organism, human or animal. Thus, a distinction is to be made between healthy organism and immunosuppressive organism.

A healthy organism, in particular human, has no congenital disease, in particular no immune weakening disease, thus having a normally working and reacting immune system.

An immune weakened organism, in particular immune weakened human, has a weakened immune system. Weakening may occur by a temporary disease, such as influenza or common cold, a long-lasting disease, such as cancer, malnourishment/undernourishment, infections with certain pathogens, as well as intake of certain medications, e.g. chemotherapeutics, or radiation. The afore-mentioned weakening is an acquired immunodeficiency which has to be distinguished from congenital immunodeficiency. Congenital immune deficiency is based on mutations in genes impairing, for example, the production or function of antibodies or phagocytes which are related to T-cell or B-cell dominated immune response.

The present invention preferably relates to an immunologically active phyto-mixture being suitable preventively or for treatment of efflorescences in healthy humans and acquired immune weakened human.

In a further embodiment, the immunologically active phyto mixture according to the invention optionally comprises additionally (d) at least one further extract of a biologically active plant comprising *Aloe* species of genus *Aloe* of the Asphodeloideae subfamily, species of genus *Stemodia* (briefly "*Stem.*") of the Plantaginaceae family and *Stem. maritima*. Preferred *Aloe* species include *Aloe vera*, *Aloe barbadensis*, *Aloe perfoliata*, *Aloe vulgaris*, *Aloe indica* and *Aloe chinensis*.

The Asteraceae family comprises the (a) genus *Bidens* (=A) comprising miscellaneous *Bidens* species also referred to colloquially as "Beggartick". Genus *Bidens* had formerly been assigned to the Compositae family by the person skilled in the art. Genus *Bidens* comprises the species *Bid. alba*, *Bid. pilosa*, *Bid. aurea*, *Bid. beckii*, *Bid. bipinnata*, *Bid. biternata*, *Bid. parviflora*, *Bid. connata* and *Bid. tripartita*. Species *Bid. alba*, *Bid. pilosa*, *Bid. bipinnata* and *Bid. parviflora* are use according the invention. Species *Bid. alba* and *Bid. pilosa* are preferred, and *Bid. alba* is particularly preferred as a plant extract in the phyto-mixture.

Distinction between the mentioned species is preferably made with young and full-grown plants having differentiated growth and which already have fruit organs, such as buds and blossoms, and leaves and blossoms differentiated in colour and shape. Preferably, one- to four-years-old, particularly preferably one- to three-years-old, plants are used.

Differentiated plants of the species *Bid. alba* and *Bid. pilosa* distinguish in growth height, wherein *Bid. alba* has a smaller maximal growth height of up to 2 m than *Bid. pilosa*. The blossoms of *Bid. alba* are small and have a radial symmetry and have an appearance similar to the daisies having yellow pollen in the center of the blossom and five, in particular white, petals. The blossoms are always arranged at the head of a twig or stem. Further features distinguishing from *Bid. pilosa* are known by the person skilled in the art.

The afore-mentioned *Bidens* species comprise flavonoids, luteolin, terpenes, polyacetylenes, phenylheptratriyne (PHT), phenylpropanoids, in particular anethole, apiol, cinnamic aldehyde, dillapiole and estragole, lipids and benzoids as secondary plant substances, and exhibit, according to the invention, antimicrobial, preferably antibacterial and/or antimycotic, as well as anti-inflammatory efficiency.

Within the meaning of the invention, the *Bidens* species according the invention, preferably *Bid. alba* and/or *Bid. pilosa*, exhibit antimicrobial, in particular at least antibacterial, efficiency against transient skin flora comprising *staphylococcus*, *streptococcus*, methicillin-resistant *Staphylococcus aureus* (MRSA), pseudomonads and/or acinetobacteria. The *Bidens* species according to the invention, preferably *Bid. alba* and/or *Bid. pilosa*, particularly preferably exhibit antibacterial efficiency against *Staphylococcus aureus* (ATCC 25923), *Staphylococcus epidermidis* (ATCC 14990), MRSA (NCTC 10442), *Pseudomonas aeruginosa* (ATCC 27853) and *Acinetobacter baumanii* (ATCC BAA 747) (Example 7).

In particular, antimicrobial, preferably antibacterial, efficiency is achieved by plant extracts of a *Bidens* species, preferably *Bid. alba* and/or *Bid. pilosa*, which comprise compounds being active against microorganisms, in particular gram-positive and/or gram-negative bacteria, comprising centaurein, centauredin, polyacetylene, phenylhepatriyne (PHT), polyyne, 1,2-dihydroxytrideca-3,5,7,9,11-pentayne.

Within the meaning of the invention, the afore-mentioned *Bidens* species exhibit, additionally to the antimicrobial, in particular antibacterial, efficiency, anti-inflammatory efficiency at less than or equal to 200±10 µg/ml of the respective plant extract, preferably less than or equal to 180±10 µg/ml, less than or equal to 160±10 µg/ml, less than or equal to 140±10 µg/ml, particularly preferably less than or equal to 130±10 µg/ml, and less than or equal to 110±10 µg/ml measured as $IC_{50}$ der 5-LOX inhibition.

In particular, anti-inflammatory efficiency is achieved by plant extracts of a *Bidens* species, preferably *Bid. alba* and/or *Bid. pilosa*, which comprise compounds being active against 5-lipoxygenase, comprising triterpenes, flavonoids, aurones, chalcones, luteolin, 1-phenyl-1,3-diyne-5-en-7-ol-acetate, caffeates and ethyl caffeates.

The Verbenaceae family, also referred to as vervain family, comprises about 35 genera. The (b) genus *Stachytarpheta* (=B) comprises the species *Sta. angustifolia*, *Sta. cayennensis*, *Sta. chamissonis*, *Sta. glauca*, *Sta. glabra*, *Sta. jamaicensis*, *Sta. indica*, *Sta. mutabilis*, *Sta. steyermarkii*, *Sta. svensonii* und *Sta. urticaefolia*. *Sta. cayennensis*, *Sta. jamaicensis* and *Sta. indica* are species within the meaning of the invention, and *Sta. jamaicensis* is particularly preferably in the phyto-mixture according to the invention as a plant extract.

The afore-mentioned *Stachytarpheta* species comprise the ingredients 3,4-dihydroxycinnamic acid (caffeic acid), flavonoids, saponins, tannins, phenols, steroids, in particular scutellarin and hispidulin, terpenes, phenylpropanoids, in particular verbascosides (also referred to as acteosides), glycosides, in particular phenylethanoid glycosides, phenylpropanoid glycosides, iridoids, iridoid glycosides, ipolamiides, tarphetalin, and 4-methoxycarbonyl-7-methylcyclopenta[c]pyran (fulvoipolamiides).

Verbascosides are phenylethanoid glycosides being an ester of phenylethanoid hydroxytyrosol, phenylethanoid 3,4-dihydroxycinnamic acid and the sugar alpha-L-rhamnopyranosyl-(1-3)-beta-D-glycopyranose.

*Stachytarpheta* species comprise the compounds verbascosides, flavonoids, glycosides, phenylethanoid and phenylpropanoid glycosides and anthraquinones as antimicrobially, preferably antibacterially and/or antimycotically, effective compounds.

*Stachytarpheta* species comprise verbascosides, flavonoids, iridoids, ipolamiides, iridoid ipolamiides, acteosides, fulvoipolamiides, sesquiterpene lactones and proazulenes as anti-inflammatorily effective compounds. Said compounds are particularly present in the leaves of the *Stachytarpheta* species according to the invention. Therefore, within the meaning of the invention, plant parts comprising the afore-mentioned compounds, in particular the leaves, are preferably used for the production of a plant extract, of *Sta. jamaicensis*, *Sta. indica* and/or *Sta. cayen-*

*nensis*. The afore-mentioned plant extract is preferably obtained as ethanolic plant extract having greater than or equal to 70% ethanol.

Surprisingly, significant anti-inflammatory efficiency has respectively been proved for *Bid. alba, Sta. jamaicensis* and *Bur. simaruba* as respective representatives of the species according to the invention of (a), (b) and (c) (Example 6, Table 2). This efficiency may be attributed to the compounds, being contained in the species according to the invention and being extracted by means of the method according the invention, comprising verbascosides, flavonoids, iridoids, ipolamiides, fulvoipolamiides, sesquiterpene lactones, polyacetylenes and/or proazulenes.

Within the meaning of the invention, the plant extracts of the *Stachytarpheta* species according the invention exhibit good antimicrobial, at least antibacterial, efficiency against transient skin flora comprising, in particular, *staphylococcus, streptococcus*, methicillin-resistant *Staphylococcus aureus* (MRSA), pseudomonads and/or acinetobacteria. *Sta. cayennensis, Sta. jamaicensis* and/or *Sta. indica* particularly exhibit antibacterial efficiency against *Staphylococcus aureus* (ATCC 25923), *Staphylococcus epidermidis* (ATCC 14990), MRSA (NCTC 10442), *Pseudomonas aeruginosa* (ATCC 27853) and *Acinetobacter baumanii* (ATCC BAA 747) (Example 7).

Within the meaning of the invention, the *Stachytarpheta* species according to the invention have, preferably, additionally to the antimicrobial, preferably antibacterial and/or antimycotic, efficiency, anti-inflammatory efficiency at less than or equal to 200±10 µg/ml of the respective plant extract, preferably less than or equal to 180±10 µg/ml, less than or equal to 160±10 µg/ml, less than or equal to 140±10 µg/ml, less than or equal to 120±10 µg/ml, particularly preferably less than or equal to 100±10 µg/ml, less than or equal to 85±10 µg/ml, less than or equal to 80±µg/ml measured as $IC_{50}$ der 5-LOX inhibition.

The Burseraceae family comprise subtribe Burserinae to which the (c) genus *Bursera* (=C) is assigned. Genus *Bursera* comprises about 100 species comprising *Bur. bipinnata, Bur. fagaroides, Bur. glabrifolia, Bur. malacophylla, Bur. microphylla, Bur. bolivarii, Bur. trifoliolata* and *Bur. simaruba. Bur. simaruba, Bur. microphylla* and/or *Bur. glabrifolia* are used within the meaning of the invention. *Bur. simaruba* is particularly preferred as a plant extract in the phyto-mixture according to the invention.

Within the meaning of the invention, the plant extracts of the *Bursera* species according the invention exhibit good antimicrobial, at least antibacterial, efficiency against transient skin flora comprising, in particular, *staphylococcus, streptococcus*, methicillin-resistant *Staphylococcus aureus* (MRSA), pseudomonads and/or acinetobacteria. *Bur. simaruba, Bur. microphylla* and/or *Bur. glabrifolia* are effective against *Staphylococcus aureus* (ATCC 25923), *Staphylococcus epidermidis* (ATCC 14990), MRSA (NCTC 10442), *Pseudomonas aeruginosa* (ATCC 27853) and *Acinetobacter baumanii* (ATCC BAA 747) (Example 7).

Within the meaning of the invention, the *Bursera* species according to the invention have, preferably, additionally to the antimicrobial efficiency, anti-inflammatory efficiency at less than or equal to 200±10 µg/ml of the respective plant extract, preferably less than or equal to 180±10 µg/ml, less than or equal to 160±10 µg/ml, less than or equal to 140±10 µg/ml, particularly preferably less than or equal to 135±µg/ml, less than or equal to 125±10 µg/ml, less than or equal to 80±10 µg/ml measured as $IC_{50}$ der 5-LOX inhibition.

Antibacterial efficiency has surprisingly been detected for *Sta. jamaicensis* and *Bid. alba*, as well as *Stem. maritima* (see Example 7). In particular, the afore-mentioned species exhibit significant efficiency against gram-positive bacteria and particularly against MRSA. Thus, the phyto-mixtures according to the invention, described herein, exhibit at least antibacterial and, preferably, additionally anti-inflammatory efficiency.

A phyto-mixture made of a plant extract of (a) *Bis. alba* and/or *Bid. pilosa* and of a plant extract of (b) *Sta. jamaicensis, Sta. cayennensis* and/or *Sta. indica* is a particularly preferred combination within the meaning of the invention. The afore-mentioned combinations surprisingly exhibit increased antibacterial as well as anti-inflammatory efficiency (Examples 2 to 8). Particularly surprisingly, double efficiency has been observed for all afore-mentioned preferred species. The experiments described herein exemplary summarize the described efficiencies for the respective species according to the invention of genus (a) *Bidens*, (b) *Stachytarpheta*, and (c) *Bursera*.

An embodiment of the phyto-mixture according to the invention comprising the respective combination of plant extracts, preferably ethanolic and dry extracts, of
(a) *Bidens alba* and/or *Bidens pilosa* and
(b) *Stachytarpheta jamaicensis*; or
(b) *Stachytarpheta jamaicensis* and
(c) *Bursera simaruba* surprisingly exhibits anti-inflammatory efficiency of less than or equal to 90±10 µg/ml, preferably at less than or equal to 70±10 µg/ml and particularly preferably at 50±10 µg/ml measured as $IC_{50}$ of 5-LOX inhibition (Table 3). The afore-mentioned phyto mixture exhibits, deviating from expectations, good antimicrobial, in particular antibacterial, efficiency at the same time (Table 5b). The other species according to the invention (a), (b), and (c) exhibit appropriate efficiencies as listed above.

An embodiment of the phyto-mixture according to the invention comprising the combination of plant extracts, preferably ethanolic and subsequently dried extracts, of
(a) *Bidens alba* and (c) *Bursera simaruba* exhibits anti-inflammatory efficiency of less than or equal to 90±10 µg/ml, preferably at less than or equal to 80±10 µg/ml measured as $IC_{50}$ of 5-LOX inhibition (Table 3). The afore-mentioned phyto mixture exhibits good antimicrobial, in particular antibacterial, efficiency at the same time. The other species according to the invention of genus (a) *Bidens* and (c) *Bursera* respectively exhibit appropriate efficiencies.

Particularly preferred combinations of (a), (b), and/or (c) comprise
i) at least one plant extract having anti-inflammatory efficiency and at least one plant extract having antimicrobial efficiency,
ii) at least one plant extract having anti-inflammatory efficiency and antimicrobial efficiency at the same time,
iii) at least one plant extract having anti-inflammatory efficiency and antimicrobial efficiency at the same time and at least one further extract of a biologically active plant (d),
wherein ethanol extracts, greater than or equal to 70% ethanol, and, in particular after drying, having a residual content of ethanol less than or equal to 5%, less than or equal to 1%, particularly preferably less than or equal to 0.1%, are respectively preferably used in each case. The implementations described above concerning the ingredients of the several plant species apply correspondingly herein.

Preferred formulations of the phyto-mixture described above and its combinations comprise tea, tincture, solution, dispersion and suspension, powder and semi-solid forms, such as ointments, creams and pastes. Tea according to the invention is based on at least one dry and ethanol-free plant extract from (a), (b), and/or (c) and, optionally, (d).

Species of genus *Stemodia* (=D1) are used as further (d) biologically active plant within the meaning of the invention. These had formerly been assigned to the Scrophulariaceae family and are nowadays assigned to the Plantaginaceae family belonging to the order Lamiales. Genus *Stemodia* (*Stem.*) comprises about 40 species comprising *Stem. maritima*, *Stem. lantana* and *Stem. durantifolia*, which are used in the meaning of the invention. *Stem. maritima* is particularly preferred.

Species of genus *Aloe* (=D2) assigned to the Asphodeloideae subfamily which belongs to the Xanthorrhoeaceae family are used as further (d) biologically active plant. Genus *Aloe* comprises about 500 species. *Aloe vera*, *Aloe barbadensis*, *Aloe albiflora*, *Aloe perfoliata*, *Aloe vulgaris*, *Aloe indica* and/or *Aloe chinensis* are preferably used according to the invention. *Aloe vera* is particularly preferred, with or without anthraquinones.

A mixture of each a plant extract from (a) *Bid. alba*, *Bid. pilosa*, (b) *Sta. jamaicensis*, *Sta. cayennensis*, *Sta. indica*, and/or (c) *Bur. simaruba*, *Bur. microphylla*, *Bur. glabrifolia*, and, optionally, (d) an *Aloe* species (D2), preferably *Aloe vera*, exhibits particularly good efficiency in topical application on the skin, mucous membrane and oral mucosa, in particular for prevention and treatment of efflorescences within the meaning of the invention. Table 1a summarizes appropriate combinations of preferred species.

TABLE 1a

| Extract combination | Preferred species | Optional preferred species of | Optional preferred species of |
|---|---|---|---|
| A-E/B-E | *Bid. alba/Sta. jamaicensis* | C-E | D1 and/or D2 |
| A-E/C-E | *Bid. alba/Bur. simaruba* | B-E | D2 = *Aloe vera* |
| B-E/C-E | *Sta. jamaicensis/Bur. simaruba* | A-E | D1 = *Stem. maritima* and, optionally, D2 |
| A-E/D1-E | *Bid. alba/Stem. maritima* | B-E | D2 |
| B-E/D1-E | *Sta. jamaicensis/Stem. maritima* | A-E | D2 |
| C-E/D1-E | *Bur. simaruba/Stem. maritima* | A-E | D2 |
| A-E/D2 | *Bid. alba/Aloe vera* | B-E | D1 |
| B-E/D2 | *Sta. jamaicensis/Aloe vera* | C-E | D1 |
| C-E/D2 | *Bur. simaruba/Aloe vera* | A-E | D1 |

Wherein A = genus *Bidens*, B = genus *Stachytarpheta*, C = genus *Bursera*, D1 = genus *Stemodia*, D2 = genus *Aloe* and E = ethanolic extract.

The amount of the at least one plant extract from (a), (b), and/or (c), and, optionally, (d) is greater than or equal to 1% by weight preferably to less than or equal to 50% by weight, preferably greater than or equal to 3% by weight, greater than or equal to 5% by weight, greater than or equal to 7% by weight to each less than or equal to 50% by weight, based on the respective dry weight (ad 100% by weight), wherein the total content of the at least one plant extract or of the combination of (a), (b), and/or (c) preferably is greater than or equal to 3% by weight, based on the total content of the phyto-mixture (ad 100% by weight), greater than or equal to 5% by weight, greater than or equal to 7% by weight to less than or equal to 50% by weight, preferably less than or equal to 30% by weight. In the case of adding a (d) *Aloe* extract (D2), the amount of D2 is preferably greater than or equal to 5% by weight, greater than or equal to 10% by weight, greater than or equal to 15% by weight, greater than or equal to 20% by weight, to each less than or equal to 70% by weight. The amounts of the other plant extracts (a), (b), and/or (c) are correspondingly low (Example 8b). The preferred amounts described herein apply correspondingly for the compositions and formulations described in the following.

In the case of combining two plant extracts, ratios of 1:1 mixtures are preferably made, as also analysed in the following examples 2 to 8. Where two plant extracts are combined, ratios may variably adjusted between 1:10 to 10:1. In the case of three or more plant extracts, ratios of 1:1:1 etc. are used. Proportions may variably adjusted, depending on availability of the material and tolerability of the patient to the respective extract. Thus, in the case of an allergy to one of the plants described herein or intolerability to one of the ingredients described above, the plant/ingredient may be excluded from the phyto-mixture. The content of the other plant extracts may be correspondingly adjusted to achieve the desired efficiency.

A further subject matter of the present invention is the immunologically active phyto-mixture according to the invention comprising at least one plant extract which exhibit antimicrobial, preferably antibacterial and/or antimycotic efficiency against transient skin flora and/or anti-inflammatory efficiency. Preferably, the phyto-mixtures according to the invention exhibit efficiency against transient skin flora and anti-inflammatory efficiency at the same time.

Within the meaning of the invention, "antimicrobial efficiency" comprises inhibition and reduction of the reproductivity, ability to divide and reproduction of microorganisms up to the inactivation or killing of microorganisms. "Antimicrobial" comprises at least antibacterial (against gram-positive and -negative bacteria) and, preferably, additionally antimycotic (against fungi and yeasts). Antimicrobial efficiency further comprises inhibition of the biosynthesis apparatus of microorganisms, such as, for example, of the synthesis of toxins, pathogenicity factors and other physiological reacts or of compounds triggering an immune response. Toxins comprises exotoxins and endotoxins, in particular exotoxins, such as the fungal toxins aflatoxin oder exofilantin A and B of *Staphylococcus aureus*.

Preferably, "antimicrobial efficiency" comprises at least one efficiency analogous to antibiotics, in particular to a lesser extent and, preferably, having less or no side effects compared to synthetic antibiotics.

Within the meaning of the invention, "transient skin flora" means a microbiological flora on/in the skin and/or mucosal membrane, which, due to impact of miscellaneous influencing factors, may cause an efflorescence, results in an efflorescence or may impair further tissues by systemic spread.

The skin flora of healthy skin comprises a "resident skin flora" which is also referred to as physiological, endogenous skin flora or "localised flora". "Resident skin flora" comprises germs, not impairing the healthy organism, comprising *staphylococcus*, in particular *Staphylococcus epidermis*, propioni-, myco- and corynebacteria. Said germs preferably multiply in *Stratum corneum* and constitute a protection flora against pathogenic and foreign microorganisms. The composition of resident skin flora may be variable for various skin regions, such as face, hands, feet, outer ear, as well as lips and oral mucosa, the skin of the eye, in particular the cornea, conjunctiva and mucous membrane of the eye.

Transient, thus temporary, skin flora comprising pathogenic germs is to be differentiated thereof. Pathogenic germs comprise gram-negative cocci, such as *Neisseria, gonococcus, meningococcus*, gram-positive cocci, such as *staphylococcus, streptococcus*, in particular *Streptococcus aureus, micrococcus, enterobacteria, pneumococcus* and *Clostridia*, gram-negative rods, such as *Bordetella, Campylobacter, Haemophilus, Heliobacter, Legionella, Salmonella, Shi-* gella, *Vibrio, Yersinia, Escherichia coli, Klebsiella, Proteus* and pseudomonads, gram-positive rods, such as *Bacillus, Clostridium, Corynebacterium, Listeria* und mycobacteria and/or yeasts, fungi, *Candida* und/oder viruses.

Healthy skin flora may be impaired by different influencing factors, such as physical, chemical, pathogenic and endogenous physiological influencing factors and merge into a transient skin flora. In particular, foreign germs or pathogenic germs may disrupt or displace healthy skin flora thus multiplying and spreading, which finally results in a skin disease. In particular diseases of the cutis, preferably of the epidermis, comprising at least one alteration of at least one tissue selected from *Stratum corneum, Stratum lucidum, Stratum granulosum, Stratum spinosum, Stratum basale* and/or *Stratum germinativum* (=*Stratum spinosum+Stratum basale*), dermis comprising *Stratum paillare* and *Stratum reticulare* and/or of the subcutis comprising connective tissue with fibroblasts, endothelial cells, collagen and fat cells.

Consequently, transient skin flora comprises, according to the invention, disordered skin flora comprising at least one of the afore-mentioned germs phenotypically causing efflorescences of at least one of the afore-mentioned tissues on the skin and oral mucosa.

Physical influencing factors comprise the afore-mentioned disruptions and impairments of the skin structure and comprise injuries, stings, cuts, scratches, abrasions, burns or chemical burns at least of the epidermis comprising *Stratum corneum, Stratum lucidum, Stratum granulosum, Stratum spinosum, Stratum basale* and/or *Stratum germinativum* (=*Stratum spinosum+Stratum basale*), optionally of the dermis comprising *Stratum paillare* and *Stratum reticulare* and/or of the subcutis comprising connective tissue with fibroblasts, endothelial cells, collagen and fat cells.

In a particular embodiment of the present invention, the immunologically active phyto-mixture according to the invention comprising at least one plant extract according to the invention (a), (b), and/or (c) and, optionally, (d) having an antimicrobial, preferably antibacterial, efficiency against transient skin flora, wherein the transient skin flora comprises *staphylococcus, streptococcus*, methicillin-resistant *Staphylococcus aureus* (MRSA), pseudomonads and/or acinetobacteria.

In a particular embodiment of the present invention, the immunologically active phyto-mixture according to the invention comprises at least one plant extract exhibiting antibacterial efficiency against at least one of the afore-mentioned germs of a transient skin flora at a concentration greater than or equal to 10 µg/ml to less than or equal to 10 mg/ml measured as minimal inhibitory concentration (MIC) and/or as minimum bactericidal concentration (MBC) of the respective plant extract or the extract mixture. Preferably, the at least one plant extract exhibit antibacterial efficiency at a concentration greater than or equal to 10 µg/ml to less than or equal to 10 mg/ml, greater than or equal to 10 µg/ml to less than or equal to 8 mg/ml, greater than or equal to 100 µg/ml to less than or equal to 8 mg/ml, greater than or equal to 250 µg/ml to less than or equal to 8 mg/ml, preferably greater than or equal to 500 µg/ml to less than or equal to 8 mg/ml, in particular greater than or equal to µg/ml to less than or equal to 6 mg/ml, greater than or equal to 100 µg/ml to less than or equal to 6 mg/ml, greater than or equal to 250 µg/ml to less than or equal to 6 mg/ml, greater than or equal to 500 µg/ml to less than or equal to 6 mg/ml, greater than or equal to 10 µg/ml to less than or equal to 4 mg/ml, greater than or equal to 100 µg/ml to less than or equal to 4 mg/ml, greater than or equal to 250 µg/ml to less than or equal to 4 mg/ml, greater than or equal to 500 µg/ml to less than or equal to 4 mg/ml.

In a particular embodiment, the phyto-mixture according to the invention with the subsequent preferred combinations of plant extracts exhibits antimicrobial, preferably antibacterial, efficiency at a concentration greater than or equal to 100 µg/ml to less than or equal to 10 mg/ml (MIC and/or MBC) comprising i) *Sta. jamaicensis, cayennensis* and/or *indica* and *Bid. alba* and/or *pilosa* ii) *Sta. jamaicensis, cayennensis* and/or *indica* and *Bur. simaruba* iii) *Sta. jamaicensis* and/or *indica* and *Bur. simaruba, Bur. microphylla* and *Bur. glabrifolia* and *Bid. alba* and/or *pilosa* and iv) 1), ii) or iii) and an *Aloe* species, respectively, and, optionally, *Stemodia maritima*.

The afore-mentioned phyto-mixtures exhibit surprisingly good efficiencies against MRSA as it is shown in Example 7 (Table 5a and 5b). Antibacterial efficiency has surprisingly been detected for chosen species (a), (b), and (c) of the plant extracts according to the invention. The same applies for the other species, according to the invention, of genus (a) *Bidens*, (b) *Stachytarpheta*, and (c) *Bursera*. The immunologically active phyto-mixture according to the invention, comprising at least one of the plant extracts according to the invention (a), (b), and/or (c) described above exhibits anti-inflammatory efficiency at less than or equal to 200±10 µg/ml, preferably at less than or equal to 180±10 µg/ml, less than or equal to 160±10 µg/ml, less than or equal to 140±10 µg/ml, less than or equal to 130±10 µg/ml, particularly preferably at less than or equal to 120±10 µg/ml measured as $IC_{50}$ of 5-LOX inhibition of the respective plant extract or the extract mixture. Particularly preferred embodiments exhibit anti-inflammatory efficiency at less than or equal to 100±10 µg/ml, preferably at less than or equal to 90±10 µg/ml, less than or equal to 80±10 µg/ml, less than or equal to 70±10 µg/ml and less than or equal to 60±µg/ml or less than or equal to 50±10 µg/ml.

Particularly preferably, the at least one plant extract exhibits anti-inflammatory efficiency at less than or equal to 90±10 µg/ml of the respective plant extract of the species according to the invention (a), (b) and/or (c).

The immunologically active phyto-mixture preferably comprises at least one plant extract selected from (a) *Bid. alba, Bid. pilosa*, (b) *Sta. jamaicensis, Sta. indica, Sta. cayennensis*, (c) *Bur. microphylla, Bur. glabrifolia* and/or *Bur. simaruba*, and, optionally, (d) as extract of the ingredients of the respective plant, preferably of the aboveground parts of the at least one plant. Preferably, the extract comprises ingredients of untainted, unaltered, freshly harvested or dried plant parts comprising bark, stem, twigs, branches, leaves, blossoms, buds, seeds, pods, pollen, fruit organs, photosynthetically active parts and/or storage organs. The extract of dried plant parts is preferred. The advantage of an extract of dried plant parts is the absence of water, thus obtaining more concentrated extracts of the respective plant. As a result, extracts having comparably higher contents of active compounds per measuring unit of the respective extract are obtained.

Consequently, plant extracts obtained according to the invention from dried plants have an increased amount of the compounds described above, preferably at least one antibacterially and/or anti-inflammatorily active compound comprising flavonoids, terpenes, benzoids, phenylpropanoids, glycosides and verbascosides, iridoids, ipolamiides, fulvoipolamiides, sesquiterpene lactones and/or proazulenes.

Within the meaning of the invention, "ingredients" comprise all of the plantal biologically and/or physiologically active compounds described herein.

In a further embodiment of the present invention, the immunologically active phyto-mixture comprises at least one plant extract selected from (a), (b), and/or (c), and, optionally, (d) which comprises each an extract of at least one of the subsequent compounds, in particular of the ingredients: flavonoids, saponins, iridoids, phenolic acids, polyphenols, polysaccharides, glycosylates, terpenes, monoterpenes, sesquiterpene lactones, proazulenes, sulfides, carotinoides, vitamins A B C D E, amino acids, and/or minerals. Particularly preferably, ethanolic, dried plant extracts of (a) Bid. alba, Bid. pilosa, (b) Sta. jamaicensis, Sta. cayennensis, Sta. indica, (c) Bur. microphylla, Bur. glabrifolia, Bur. simaruba and/or (d) Stem. maritima have one of the afore-mentioned compounds.

In a particular embodiment of the immunologically active phyto-mixture according to the invention, it comprises at least one plant extract selected from (a), (b), and/or (c), and, optionally, (d) which comprises at least one of the antimicrobially, preferably antibacterially, effective compounds verbascosides, flavonoids, glycosides, phenylethanoid glycosides, phenylpropanoid glycosides and/or anthraquinones. Preferably, the afore-mentioned phyto-mixture comprises at least one plant extract from (b) St. jamaicensis, Sta. cayennensis, Sta. indica, (a) Bid. alba and/or Bid. pilosa.

In a further embodiment of the immunologically active phyto-mixture according to the invention, it comprises at least one plant extract selected from (a), (b), and/or (c), and, optionally, (d) which comprises at least one of the anti-inflammatorily effective compounds verbascosides, flavonoids, iridoids, ipolamiides, fulvoipolamiides, sesquiterpene lactoces and or proazulenes. Preferably, the afore-mentioned phyto-mixture comprises at least one plant extract from (b) St. jamaicensis, Sta. cayennensis, Sta. indica, (a) Bid. alba and/or Bid. pilosa.

In a particular embodiment of the immunologically active phyto-mixture according to the invention, it comprises at least two of the afore-mentioned plant extracts selected from (a), (b), and/or (c), and, optionally, (d) preferably comprising at least one of the species (b) St. jamaicensis, Sta. cayennensis and/or Sta. indica, and one of the species (a) Bid. alba and/or Bid. pilosa which comprise extracts, preferably ethanolic extracts, of the afore-mentioned ingredients.

The plant extracts according to the invention described above, phyto-mixtures comprising the plant extracts and embodiments according to the invention are provided for the production as medicament, medical product, nutritional supplement and cosmetic. The phyto-mixture is present in different forms for these purposes.

Therefore, a further subject matter of the invention is the immunologically active phyto-mixture according to the invention, wherein the at least one plant extract (a) Bid. alba, Bid. pilosa, (b) Sta. jamaicensis, Sta. indica, Sta. cayennensis, (c) Bur. microphylla, Bur. glabrifolia and/or Bur. simaruba, and, optionally, (d) is present in
 liquid form comprising solution, dispersion, suspension, emulsion, tincture, syrup, juice, and tea
 solid form comprising tablet, powder, powder, dragee, globules, granules and lyophilisate, in particular freeze-dried form, or
 as mixture comprising capsules, aerosol, spray, emulsion, lotion, and cream.

In an embodiment of the immunologically active phyto-mixture, the at least one plant extract or the phyto-mixture according to the invention in liquid form, preferably tincture, solution, dispersion and/or suspension, each alternatively has a pH tolerated by the skin greater than or equal to 3 to less than or equal to 9, a pH tolerated by the oral mucosa greater than or equal to 6 to less than or equal to 8, a pH tolerated by the nasal mucosa greater than or equal to 5 to less than or equal to 7, or a pH tolerated by the eye greater than or equal to 7 to less than or equal to 9.

Subsequent to the production of the plant extract according to the invention, in particular of the phyto-mixture, according to the method according to the invention, the direct product is present in freeze-dried form, preferably as lyophilisate, after freeze-drying. Subsequently, it may be processed into fine powders, tablets or liquid forms.

In an embodiment, the liquid immunologically active phyto-mixture according to the invention is present as tincture, in particular as solution, suspension or dispersion, comprising
 greater than or equal to 1% by weight, preferably greater than or equal to 3% by weight, greater than or equal to 5% by weight, greater than or equal to 7% by weight, of at least one plant extract selected from (a) Bid. alba, Bid. pilosa, B) Sta. jamaicensis, Sta. cayennensis, Sta. indica, and/or (c) Bur. simaruba, Bur. microphylla, Bur. glabrifolia, based on the total content of the tincture (T=100% by weight),
 at least one acidifier comprising acetic acid, citric acid, ascorbic acid, adipic acid, tartaric acid, mandelic acid, and/or malic acid,
 greater than or equal to 1% by weight, preferably greater than or equal to 3% by weight, greater than or equal to 5% by weight, greater than or equal to 10% by weight, greater than or equal to 15% by weight, of an Aloe extract, based on the total content of the tincture (T=100% by weight),
 wherein the tincture has a pH value of greater than or equal to 3 to less than or equal to 9 and the tincture is an aqueous/ethanolic mixture having an ethanol concentration greater than or equal to 70%, based on the total composition of the tincture (e.g. Example 8b). The total content of the plant extract or of the combination of each a plant extract (a), (b) and/or (c), respectively, preferably is greater than or equal to 3% by weight, preferably greater than or equal to 5% by weight, greater than or equal to 7% by weight, respectively based on the phyto-mixture (ad 100% by weight).

All physiologically compatible, synthetic, biobased and natural acidifiers are suitable as acidifiers. In particular, acidifiers being available as foodstuffs, such as vinegar, cider vinegar, white vine vinegar, balsamic vinegar, may be used as acidifiers. Ultrapure, pharmaceutically and/or cosmetically authorised acidifiers are preferably used.

The appropriate pH value of the respective phyto-mixture depends on the type of indication and its administration form. The acidifier is suitable for setting the pH value, without limiting it to this function. The pH value is greater than or equal to 3 to less than or equal to 9, preferably greater than or equal to 3.1, greater than or equal to 3.2, greater than or equal to 3.5 to each less than or equal to 8.7, less than or equal to 8.5 8.3 8.1 7.9, less than or equal to 7.8 and preferably less than or equal to 7.6.

Topical formulations, preferably solution, dispersion, suspension, tincture, aerosol, spray and/or semi-solid formulations, such as ointment, cream and paste, for application on the skin within the meaning of the invention, excluding oral/nasal mucosa, eye, cornea, conjunctiva and mucous membrane of the eye, comprising the phyto-mixture according to the invention comprising at least one plant extract (a), (b), and/or (c), and, optionally, (d), preferably have a pH greater than or equal to 3 to less than or equal to 9, preferably greater than or equal to 3.5 to less than or equal to 8.7, less than or equal to 8.5 8.3 8.1 7.9. In particular, respectively pH 3.2 3.4 3.6 3.8 4.0 4.2 4.4 4.6 4.8 5.0 5.2 5.3 5.4 5.5 5.6 5.7 5.8 5.9 6.0 6.2 6.4 6.6 6.8 7.0 7.2 7.4 7.6 7.8 8.0 8.1 8.3 8.5 or 8.7.

Formulations according to the invention (Example 8a-b) for application on the outer ear and ear canal, preferably solution, dispersion, suspension, tincture, spray, aerosol and semi-solid formulations, respectively have a pH greater than or equal to 3 to less than or equal to 9, preferably greater than or equal to 4 to less than or equal to 7.

Formulations according to the invention (Example 8a-b) for application on the oral mucosa, preferably solution, dispersion, suspension, tincture, spray, aerosol and semi-solid formulations, respectively have a pH of preferably greater than or equal to 6 to less than or equal to 8, preferably greater than or equal to 6.2 to less than or equal to 7.8. In particular 6.2 6.3 6.4 6.5 6.6 6.5 6.6 6.7 6.8 6.9 7.0 7.1 7.2 7.3 7.4 7.5 or 7.6.

Formulations according to the invention for depositing on the nasal mucosa, preferably tincture, solution, dispersion, suspension, spray, aerosol and semisolid formulations, respectively have a pH of preferably greater than or equal to 5 to less than or equal to 7. In particular pH 5.1 5.2 5.3 5.4 5.5 5.5 5.6 5.7 5.8 5.9 6.0 6.1 6.2 6.3 6.4 6.5 6.6 6.5 6.6 6.7 6.8 6.9 or 7.0.

Formulations according to the invention, preferably solution, dispersion, suspension and tincture, for applying on/in the eye, in particular on the cornea, conjunctiva and mucous membrane of the eye, respectively have a physiological pH, preferably greater than or equal to 7 to less than or equal to 9. In particular pH 7.1 7.2 7.3 7.4 7.5 7.5 7.6 7.7 7.8 7.9 8.0 8.1 8.2 8.3 8.4 or 8.5.

The pH values described above and preferred pH ranges for the respective use correspondingly apply for all described embodiment of the phyto-mixture according to the invention and of the formulations comprising at least one plant extract (a), (b), and/or (c), and, optionally, (d), without explicitly stating it.

A further embodiment of the immunologically active phyto mixture according to the invention comprises, in solid form, at least one essentially at least one essentially dry, in particular solvent-free, plant extract, selected from (a) *Bid. alba, Bid. pilosa*, (b) *Sta. indica, Sta. jamaicensis, Sta. cayennensis*, and/or (c) *Bur. simaruba, Bur. microphylla, Bur. glabrifolia*, and, optionally, (d) *Stemodia maritima*, and/or an *Aloe* species.

Within the meaning of the invention, "essentially dry" means that the respective plant extract (a), (b), and/or (c), and, optionally, (d) of the at least one plant has a residual moisture of less than or equal to 10% by weight, preferably less than or equal to 8% by weight, less than or equal to 5% by weight, less than or equal to 4% by weight, less than or equal to 3% by weight, less than or equal to 2% by weight, particularly preferably less than or equal to 1% by weight, less than or equal to 0.1% by weight, equal to 0% by weight, based on the total weight of the respective plant extract.

Within the meaning of the invention, "solvent-free" means a residual content of solvent less than or equal to 10% by weight, preferably less than or equal to 8% by weight, less than or equal to 5% by weight, less than or equal to 4% by weight, less than or equal to 3% by weight, less than or equal to 2% by weight, less than or equal to 1% by weight, particularly preferably less than or equal to 0.1% by weight, based on the total weight of the respective plant extract of the at least one plant, wherein solvents comprise water, 1,2-propylene glycol, aqueous ethanol, ethanol, in particular greater than or equal to 70% ethanol to less than or equal to 100% ethanol, greater than or equal to 70% ethanol, methanol, acetone, chloroform, n-butanol, hexane, ethyl acetate, diethyl ether, or a mixture of at least two of the aforementioned solvents. Solvents, being completely removable, in particular without harmful or irritating residuals, are preferred.

A further subject matter of the present invention is a method for the production of an immunologically active phyto-mixture comprising at least one plant extract respectively selected from the species according to the invention of genus (a) *Bid. alba, Bid. pilosa*, (b) *Sta. jamaicensis, Sta. cayennensis, Sta. indica*, (c) *Bur simaruba, Bur. microphylla* and/or *Bur. glabrifolia*, and, optionally, (d) *Stemodia* and/or *Aloe*, respectively, comprising the steps of providing at least one plant part of at least one plant selected from above- and/or underground plant parts, in particular bark, stem, twigs, branches, leaves, blossoms, buds, seeds, pods, pollen, fruit organs, photosynthetically active parts, storage organs and/or root, at least one extraction step, in particular at least one cycle of the method comprising at least one extraction step, at least one separating step and, optionally, at least one drying step, and obtaining at least one plant extract, preferably in dry or liquid form, and optionally, a further processing step comprising drying, crushing, milling by means of a mill, processing in a mortar, dispersing, and/or optionally, processing into a homogenous mixture.

In the separating step, the obtained extract is separated from the remaining plant parts using the solvent, preferably by filtration, thin-layer chromatography, distillation, shaking out or evaporation. Choice of the separating step is knowledge of the person skilled in the art.

Remaining and separated plant parts may subsequently be supplied to another extraction and be previously crushed if required. The steps extraction, separating, optionally drying of the obtained extract and crushing of separated plant parts may, in a variable manner, be combined, joined with fresh plant parts and repeated. The arrangement of the method is knowledge of the person skilled in the art, achieving maximal yield of the ingredients already described above in the plant extract according to the invention (a), (b), and/or (c), and, optionally, (d), and the phyto-mixture according to the invention.

Preferably, plant parts of the plants are used, selected from
(a) *Bid. alba*,
(b) *Sta. jamaicensis*, and/or
(c) *Bur. simaruba*, and, optionally,
(d) genus *Aloe* ad/or genus *Stemodia*, preferably *Stem. maritima, Aloe vera, Aloe barbadensis, Aloe perfoliata, Aloe vulgaris, Aloe indica* and/or *Aloe chinensis*.

One cycle of the method comprises at least one extraction step and at least one separating step. Optionally, at least one drying step of the already obtained extract may be performed between cycles. Drying step of the separated plant parts may be performed if required. In the case of using a toxic solvent a further step for removing the solvent is preferably performed.

In an embodiment of the method according to the invention, undesired ingredients of the respective plant extract according to the invention (a), (b), and/or (c), and, optionally, (d) are removed. Preferably, compounds with laxative effect, in particular anthraquinones, are removed for oral formulations for absorption through the gastrointestinal tract.

Preferably, the at least one further processing step for homogenization of the obtained liquid or dry plant extract is performed prior to mixing of the at least two plant extracts or prior to the formulation into one of the administration forms described herein (Example 8a-b) of the phyto-mixture according to the invention.

In the method according to the invention for the production of an immunologically active phyto-mixture comprising at least one plant extract according to the invention (a), (b), and/or (c), and, optionally, (d), extraction is performed with at least one solvent, comprising water, 1,2-propylene glycol, aqueous ethanol, ethanol, greater than or equal to 70% ethanol to less than or equal to 100% ethanol, methanol, acetone, chloroform, n-butanol, hexane, ethyl acetate, and/or diethyl ether in particular a mixture of at least two of the afore-mentioned solvents.

Aqueous ethanol greater than or equal to 70% ethanol to less than or equal to 100% ethanol is preferably used as solvent for extraction. Due to low to no toxicity of ethanol, the aqueous extracts and ethanol extracts of the species according to the invention (a), (b), and/or (c), and, optionally (d) are preferred in contrast to, for example methanol, acetone or chloroform. After drying, the residual content of ethanol preferably is less than or equal to 5%, particularly preferably less than or equal to 1%, less than or equal to 0.1% of ethanol. Aqueous ethanol, ethanol, preferably greater than or equal to 70% to less than or equal to 100% are preferred solvents. In particular greater than or equal to 75%, greater than or equal to 80%, greater than or equal to 85%, greater than or equal to 90%, greater than or equal to 95%, 96%, 97%, 98% to less than or equal to 100% ethanol. Particularly preferably, Ultrapure and biobased ethanol is used.

In a preferred embodiment of the method according to the invention for the production of an immunologically active phyto-mixture within the meaning of the invention, at least one plant extract (a), (b), and/or (c), and, optionally, (d) is obtained in liquid form, in dry form or as mixture of solid and liquid forms.

In context of the obtained product according to the method according to the invention, "mixture" comprises dry and liquid ingredients extracted from the plant parts. Liquid ingredients may comprise residual moisture of the liquids from the plants, oily ingredients and residual solvent.

The method according to the invention for the production of at least one immunologically active phyto-mixture further comprises at least one mixing step, comprising
i) mixing at least two of the plant extracts according to the invention selected from (a), (b), and/or (c), in particular in liquid form, in dry form and/or as mixture of solid and liquid forms, or
ii) mixing at least one of the plant extracts according to the invention selected from (a), (b), and/or (c), in particular in liquid form, in dry form and/or as mixture of solid and liquid forms, with (d) at least one further extract of a biologically active plant, and
in particular a step for homogenization, dispersion of the at least one plant extract prior to mixing, and
obtaining of the phyto-mixture according to the invention.

In an arrangement of the method according to the invention, a dried form of at least one plant extract, e.g. a powder, with a liquid form of at least one plant extract can be mixed. The liquid form may be, for example, an undried ethanol extract. The advantage is that the concentration of the total plant extract per volume is not reduced by additional liquids. Moreover, purity of the extract is improved since mixtures of solvents are avoided and defined concentrations and mixtures are produced.

Preferably, dry forms of extracts are mixed into an immunologically active phyto mixture comprising at least one plant extract according to the invention (a), (b), and/or (c) and subsequently processed into a liquid form, preferably solution, solution for use as tincture, tincture, suspension and/or dispersion, using a solvent, preferably ultrapure ethanol. Preferably, a phyto-mixture according to the invention made of dry extracts according to the method according to the invention is obtained, comprising
providing at least one plant part, respectively, of
(a) *Bidens alba* and/or *Bidens pilosa*,
(b) *Sta. jamaicensis*, *Sta. cayennensis* and/or *Sta. indica*,
(c) *Bur. simaruba*, *Bur. microphylla* and/or *Bur. glabrifolia*, and, optionally, (d) an *Aloe* species selected from *Aloe vera*, *Aloe barbadensis*, *Aloe perfoliata*, *Aloe vulgaris*, *Aloe indica* and *Aloe chinensis*,
respectively, extraction of the afore mentioned plant parts of (a), (b), and/or (c), and, optionally, (d) using a described, appropriate solvent, in particular at least one extraction step and preferable each at least one cycle of the method,
respectively obtaining at least one plant extract of (a), (b), and/or (c), and, optionally, (d) comprising at least one appropriate solvent, and
drying the respectively obtained plant extract, preferably by freeze-drying,
optionally, repeating of the extraction step of the remaining plant parts
optionally, a further processing step comprising drying, crushing, milling by means of a mill, processing in a mortar, dispersing, and
mixing of the obtained, dry, preferably fine, plant extracts (a), (b), and/or (c), and, optionally, (d),
obtaining of an immunologically active phyto-mixture in dry form, and
adding greater than or equal to 70% to less than or equal to 100% ethanol, preferably greater than or equal to 75%, greater than or equal to 80%, greater than or equal to 85%, greater than or equal to 90%, greater than or equal to 95%, 96%, 97%, 98% to less than or equal to 100% ethanol, particularly preferably ultrapure ethanol or biobased ultrapure ethanol, and
obtaining at least 70% ethanolic solution, in particular suspension, tincture or dispersion, based on 100 ml total volume (ad 100%), (Example 8b).

In an alternative of the method described above, the extraction is performed with a respectively appropriate solvent and this is subsequently removed and the plant extract is dried. In order to produce a solution, dispersion, suspension or tincture, the dried and solvent-free plant extract is not homogenously mixed in ethanol, but in an aqueous solvent without ethanol. The advantage is that no irritating solvent is contained in the case of application on the skin or mucous membrane, in particular on wounds. The "aqueous alternative" correspondingly applies for all formulations according to the invention and indications. In particular for formulations for application in the eye, on nasal und oral mucosa.

"Aqueous solvents" shall be understood to mean physiologically, pharmaceutically compatible solutions on the basis of water or physiologically compatible buffer systems, in which the dried plant extracts are homogenously mixable into a dispersion or solution. The person skilled in the art knows such "aqueous solvents". Preferably plant extracts are mixed which are obtained by the method according to the invention from plant parts of plants selected from
(a) *Bid. alba* or *Bid. pilosa*,
(b) *Sta. jamaicensis, Sta. cayennensis* or *Sta. indica*, and/or
(c) *Bur. simaruba, Bur. microphylla* or *Bur. glabrifolia*, and, optionally
(d) at least one species of genus *Aloe* and/or *Stemodia*, preferably *Stem. maritima, Aloe vera, Aloe barbadensis, Aloe perfoliata, Aloe vulgaris, Aloe indica* and/or *Aloe chinensis*.

A further subject matter of the present invention is an immunologically active phyto-mixture obtained by the method described above, wherein the phyto-mixture comprises at least one plant extract selected from the species according to the invention of genus (a) *Bid. alba, Bid. pilosa*, (b) *Sta. jamaicensis, Sta. cayennensis, Sta. indica*, (c) *Bur. simaruba, Bur microphylla* and/or *Bur. glabrifolia*, and, optionally, (d) at least one further extract of a further biologically active plant, preferably of genus *Aloe* and/or *Stemodia*, particularly preferably *Stem. maritima* and/or of at least one *Aloe* species.

Explanations on ingredients, anti-inflammatory and anti-microbial, preferably antibacterial, efficiencies correspondingly apply for the method according to the invention and the direct products obtained by means of the method. Thus, the products obtained according to the described method exhibit the efficiencies described above, as shown by examples 2 to 9.

A further subject matter of the present invention is an immunologically active phyto-mixture in the manner described above and/or produced according to the method described above comprising at least one plant extract selected from the species respectively according to the invention of genus (a) *Bidens*, (b) *Stachytarpheta*, and/or (c) *Bursera*, and, optionally, (d) at least one further extract of a further biologically active plant for use as medicament, medical product, nutritional supplement, cosmetic, and/or as an immunologically active addition to one of the afore-mentioned products.

All described formulation according to the invention are suitable as or for the production of medicaments, medical products, nutritional supplements and cosmetics.

"Nutritional supplements" preferably comply, according to the invention, with EU directive 2002/46/EG and comprise products for increased supply of the human body, preferably as powder, tablet or tea, each comprising the immunologically active phyto-mixture comprising at least one plant extract according to the invention (a), (b), and/or (c), and, optionally, (d), or a preferred embodiment of the phyto-mixture.

Within the meaning of the invention, "medical products" are the formulations described herein comprising the described immunologically active phyto-mixture comprising at least one plant extract according to the invention (a), (b), and/or (c), and, optionally, (d) for use in the prevention or treatment of human for medically therapeutic purposes. The medical products according to the invention preferably comply with the directive 93/42/EWG. Examples include medicinal tea, drops, tincture, ointment, cream and paste comprising the phyto-mixture. Within the meaning of the invention, "cosmetics" are topical cosmetic products for depositing on the skin comprising the phyto-mixture according to the invention comprising at least one plant extract according to the invention (a), (b), and/or (c), and, optionally, (d). Such cosmetic products include cream, soap, peeling, poultice, cleansing solution or mil, and related skin care products.

Therefore, a further subject matter of the present invention is a pharmaceutic or cosmetic composition comprising the immunologically active phyto-mixture according to the invention that comprises at least one plant extract according to the invention selected from (a) genus *Bidens* of the Asteraceae family, (b) genus *Stachytarpheta* of the Verbenaceae family, and/or (c) genus *Bursera* of the Burseraceae family, and, optionally, (d) at least one further extract of a further biologically active plant comprising *Aloe* species of genus *Aloe* of the Asphodeloideae subfamily, species of genus *Stemodia* of the Plantaginaceae family and/or *Stemodia maritima*. Preferably, the afore-mentioned compositions comprise at least one cosmetically and/or pharmaceutically authorised excipient. The described preferred embodiments of the phyto-mixture and the formulations correspondingly apply for the pharmaceutic or cosmetic composition.

A further subject matter of the present invention is an immunologically active-phyto mixture, preferably a composition comprising the phyto-mixture, for use in the prevention or in a method for treatment of efflorescences comprising at least one plant extract according to the invention selected from
(a) *Bid. alba, Bid. pilosa*,
(b) *Sta. jamaicensis, Sta. cayennensis, Sta. indica*, and/or
(c) *Bur. simaruba, Bur. microphylla* and/or *Bur. glabrifolia*, and, optionally,
(d) genus *Aloe* of the Asphodeloideae subfamily, genus *Stemodia* of the Plantaginaceae family, preferably *Stemodia maritima, Aloe vera, Aloe barbadensis, Aloe perfoliata, Aloe vulgaris, Aloe indica* and/or *Aloe chinensis*.

In general, "Efflorescences" are skin alterations and comprise cosmetic efflorescences occurring without health-damaging impairment of human, but are pertinent to psychological well-being of human, and physiologically pathologic efflorescence causing health-damaging impairment right up to serious and life-threatening diseases, such as skin cancer, in humans and animals.

Cosmetic efflorescences comprise superficial scratches in the skin, in particular epidermis, irritations or abrasions of the skin surface, tearing of the skin and roughness each of the skin, in particular epidermis.

Pathologic efflorescences comprise skin diseases accompanying with an inflammatory reaction of at least one tissue of the skin and/or comprising microbial, in particular bacterial, infection. Pathologic efflorescences are also summarized as such skin alterations that originally occur as cosmetic efflorescence and evolve into pathologic efflorescences in the course of disease, in particular through changes in the constitution of the skin cells.

According to the invention, "efflorescences" comprise irritations and inflammations of skin and mucous membrane, bacterial infections, bacterial infections accompanying with viral infections, mycoses, after-effects and secondary infection of infectious and parasitic diseases, diseases of the outer ear, Otitis extema (H60., H62.1, H62.2 ICD-10-GM), abscess of the outer ear (H60.0 ICD-10-GM), furuncle of the outer ear, local infections of skin and subcutis, Impetigo (L01.-ICD-10-GM), skin abscesses, furuncles and carbuncles (L02.-, L02.0 bis L02.9 ICD-10-GM), inflammations of the skin accompanying with pilonidal cyst (L05.-), erythrasma (L08.1 ICD-10-GM), bullous dermatoses (L10-L14), dermatitis and eczemas (L20-L30), diaper dermatitis (L22), allergic contact dermatitis (L23), toxic dermatitis (L24), pruritus (L29.-), other dermatitis (L30- to L30.09), Lichen *ruber* (L43.-), papulosquamous skin diseases (L45), urticaria und erythema (L50-54), symptoms affecting the skin and the subcutaneous tissue, burns, chemical burns, diseases of the skin and the subcutis through exposure to radiation (L55-L59) including sunburn, Dermatitis solaris acuta 1. to 2. degree (L55), frostbites, complications trough medical and surgical treatment and impairments accompanying therewith comprising wound healing, scars and wounds.

The abbrevation "ICD-10-GM" stands for "International Statistical Classification Of Diseases And Related Health Problems, 10th revision, German Modification" (ICD-10-GM) and is regularly updated. Herewith, explicit reference is made to this classification and to the description of skin diseases and, in particular, the content of chapter XII, L00-L59 is incorporated into the disclosure of the present invention.

Within the meaning of the invention, "skin" comprises the skin of the limbs, of the extremities, of the joints, of the upper head, of the head, of the outer ear, nose, nasal mucosa, as well as lips and oral mucosa, and the skin of the eye, in particular the cornea, conjunctiva and mucous membrane of the eye. In particular, "skin" comprises at least one tissue layer comprising *Stratum corneum, Stratum lucidum, Stratum granulosum, Stratum spinosum, Stratum basale* and/or *Stratum germinativum* (=*Stratum spinosum*+*Stratum basale*), optionally of the dermis comprising *Stratum papillare* and *Stratum reticulare* and/or of the subcutis comprising conjunctive tissue with fibroblasts, endothelial cells, collagen and fat cells.

Preferably, the immunologically active phyto-mixture, preferably the composition comprising the phyto-mixture, is used for use in the prevention or in a method for treatment of the afore-mentioned efflorescences, wherein the at least one plant extract is selected from
  (a) *Bid. alba, Bid. pilosa*,
  (b) *Sta. jamaicensis, Sta. cayennensis, Sta. indica* and/or
  (c) *Bur. simaruba, Bur. microphylla* and/or *Bur. glabrifolia*, and, optionally,
  (d) an *Aloe* species of genus *Aloe* and/or of genus *Stemodia*, preferably *Stem. maritima, Aloe vera, Aloe barbadensis, Aloe perfoliata, Aloe vulgaris, Aloe indica* and/or *Aloe chinensis*. A topical formulation, such as tincture, solution, suspension, dispersion, powder, ointment, paste or cream is preferred (see Example 8a-b).

Preferably, the immunologically active phyto-mixture for use in the prevention or in a method for treatment of efflorescences, as described above, comprises as (d) at least one further extract of a biologically active plant of at least one *Aloe* species of genus *Aloe* comprising *Aloe vera, Aloe barbadensis, Aloe perfoliata, Aloe vulgaris, Aloe indica* or *Aloe chinensis, Aloe vera*, a species of genus *Stemodia* and/or *Stemodia maritima*.

In a preferred arrangement of use of the immunologically active phyto-mixture according to the invention, preferably of the composition comprising the phyto-mixture, for prevention or in a method for treatment of efflorescences, efflorescences comprise cosmetic or pathologic efflorescences, skin diseases associated with the transient skin flora, bacterial and/or viral infections of the skin, furunculoses, mycoses, inflammatory reactions of the skin, impetigo, benign and malign tumor formation, dermatoses, eczemas, pruritus, psoriasis, acne, skin irritations, erythema, symptomatical efflorescences, burns, chemical burns, frostbites, efflorescences occurring by toxins, medicaments, drugs, allergens, radiation and as side effect, irritations and inflammations of the skin caused by bites and stings of insects and parasites. In particular efflorescences according to ICD-10-GM.

Efficiency of the phyto-mixture according to the invention in some of the efflorescences using the formulations according to the invention is described in Example 9 and in Table 7, without being limited to them.

The immunologically active phyto-mixture, preferably the composition comprising the phyto-mixture, for use in the prevention or in a method for treatment of efflorescences within the meaning of the invention preferably comprises at least one excipient selected from fillers, accelerators for disaggregation, lubricants, disintegrants, greases, release agents, glidants, solvents, emulsifiers, solubilizing agents, solubilizers, wetting agents, salt forming agents, buffer, gel forming agents, thickening agents, film forming agents, binders, sorbents, sweeteners, colorants, plasticizers, stabilizers, matrix forming agents, polymers, acidifiers, preservatives, scents and/or retarding agents.

Each formulation according to the invention (Examples 8a and 8b), preferably of the composition comprising the immunologically active phyto-mixture, may comprise excipients known from the state of the art. Further excipients comprise carriers, preservatives, antioxidants, stabilizers, vitamins, colorants, smell improving agents and flavors.

Flavors serve for masking a potentially unpleasant taste of the phyto-mixture, in particular of the formulation comprising the afore-mentioned phyto-mixture. For example, mint, anise, fennel, menthol, caraway, medicinal honey, honey, agave juice, sugar, sugar substitute as well as sugar replacer, propolis, and other flavors and flavourings known according to the state of the art, are well suited hereto. In cosmetic formulations, preferably of the composition comprising the phyto-mixture, comprising the immunologically active phyto-mixture from (a), (b), and/or (c), and, optionally, (d), such as ointment, paste, cream and gel, animal and vegetable fats, waxes, paraffins, starch, tragacanth, cellulose derivatives, polyethylene glycols, silicons, bentonites, silicic acid, talcum, and zinc oxide, or mixtures of at least two of the afore-mentioned substances may be used as excipients.

Excipients for powder or sprays comprising the immunologically active phyto-mixture from (a), (b), and/or (c), and, optionally, (d) comprise lactose, talcum, silicic acid, aluminium hydroxide, calcium silicate, calcium and magnesium carbonate, magnesium oxide, metal soaps, cellulose powder, pure and modified starches and polymer powder, polyamide powder, or mixtures of at least two of the afore-mentioned substances. Sprays and aerosols may additionally comprise common propellants, e.g. hydrochlorfluorocarbons, propane/butane or dimethylether, wherein preferably biologically and pharmaceutically compatible propellants are used. Powder preferably comprise lactose, silicic acid, calcium silicate and/or mineral ash, e.g. from grain.

Solutions, dispersions, suspensions and emulsions comprising the immunologically active phyto-mixture from (a), (b), and/or (c), and, optionally, (d) may comprise common excipients, such as solvents, solubilizing agents and emulsifiers, e.g. water, ethanol isopropanol, ethylcarbonate, ethylacetate, benzylalcohol, benzylbenzoate, propylene glycol, 1,3-butylglycol, oils, cottonseed oil, peanut oil, maize germ oil, olive oil, castor oil and sesame oil, glycerin fatty acid ester, polyethylene glycol and fatty acid esters of sorbitan, or mixtures of at least two of the afore-mentioned substances.

Suspensions comprising the immunologically active phyto-mixture form (a), (b), and/or (c), and, optionally, (d) comprise common excipients, such as liquid diluents, e.g.

water, ethanol or propylene glycol, suspension agents, e.g. ethoxylated isosterylalcohols, polyoxyethylene sorbitol ester and polyoxyethylene sorbitan ester, microcrystalline cellulose, aluminium metahydroxide, bentonite, agar agar, and tragacanth, or mixtures of at least two of the aforementioned substances.

Soaps comprising the immunologically active phyto-mixture form (a), (b), and/or (c), and, optionally, (d), which comprise excipients, such as alkali salts of fatty acids, salts of fatty acid semi-esters, fatty acid protein hydrolysates, isothionates, lanolin, fatty alcohol, plant oils, plant extracts, glycerin, sugar, or mixtures of at least two of the aforementioned substances, are particularly well suited for daily use.

Preferred excipients for formulations of medical products in solid or liquid form for prevention or treatment of efflorescences within the meaning of the invention comprise lactose, sucrose, dextrose, mannitol, sorbitol, starch, gelatin, tragacanth, pectin, cellulose, methylcellulose, hydroxypropylmethylcellulose (HPMC), carboxymethylcellulose sodium, ethylcellulose, hydroxypropylmethylcellulose phthalate, cellulose acetate phthalate, polyvinylpyrrolidone, polyvinylalcohole, polyacrylic acid, polyethylene glycol, polyethylen oxide, sodium dodecylsulfate, sodium acetylstearylsulfate, and/or sodium dioctylsulfosuccinate (also K salts, Ca salts).

Preferred excipients for tinctures, solutions, dispersions and suspensions according to the invention comprising the immunologically active phyto-mixture from (a), (b), and/or (c) and, optionally, (d) comprise dextrose, mannitol, tragacanth, pectin, methylcellulose, hydroxypropylmethylcellulose (HPMC), carboxymethylcellulose sodium, polyvinylpyrrolidone, polyvinylalcohole, polyacrylic acid, polyethylene glycol, polyethylene oxide, sodium dodecylsulfate, sodium acetylstearylsulfate and/or Na-dioctylsulfosuccinate (also K salts, Ca salts), and, in particular for suspensions, also cellulose.

Semisolid forms or mixtures comprising the immunologically active phyto-mixture form (a), (b), and/or (c), and, optionally, (d) comprise hydroxypropylmethylcellulose (HPMC), carboxymethylcellulose sodium, polyethylene glycol, polyethylene oxide, sodium dodecylsulfate, sodium acetylstearylsulfate and/or pectin.

In a particular arrangement of the immunologically active phyto-mixture according to the invention comprising at least one plant extract from (a), (b), and/or (c), and, optionally, (d), preferably the composition comprising the phyto-mixture, for use in the prevention or in a method for treatment of efflorescences within the meaning of the invention, the phyto-mixture according to the invention is present as
 oral formulation comprising 1) solid forms, such as tablet, powder, granules, effervescent tablet, dry syrup, dragee, globules, capsule and lyophilisate, ii) liquid forms, such as suspension, solution, dispersion, tincture, concentrate, tea, or iii) mixture, such as spray, or
 topical formulation comprising 1) solid forms, such as powder, bath additive, hip bath powder, ii) liquid forms, such as suspension, solution, dispersion, tincture, tea, or iii) mixture, such as spray, aerosol, lotion, semi-solid forms comprising ointments, creams and pastes.

Within the meaning of the invention, tablets comprise simple tablets, lozenges, sublingual and buccal tablets, oral dispersible tablets, solution tablets, microtablets, chewable tablets and effervescent tablets, spot tablet, scaffold tablet and multi-layer tablet, dragees and pellets. In the case of dissolution in mouth and oral mucosa the 15 pH value preferably is in the described pH ranges.

In context of a formulation (Example 8a and 8b), mixtures comprise semi-solid forms. Semi-solid forms of medicaments and cosmetic products include ointment-like preparations, characterised by having limited form stability. Ointments and creams include all spreadable preparations being applied on the skin or mucous membrane. Depending on character, semi-solid forms are distinguished in ointments, creams, pastes or gels.

Ointments, in narrower sense, include preparations without aqueous phase. Hydrophobic, hygroscopic and hydrophilic ointments are distinguished. Creams are ointments comprising an aqueous phase beside a lipid phase. Pastes are highly concentrated suspension ointments, representing the physical-chemical transition from suspensions to moist powders.

Preferably, the immunologically active phyto-mixture according to the invention comprising at least one plant extract according to the invention from (a), (b), and/or (c), and, optionally, (d), preferably the composition comprising the phyto-mixture, for use in the prevention or in a method for treatment of efflorescences within the meaning of the invention is present as tincture, in particular as solution, suspension, dispersion or in semi-solid form (Example 9), comprising
 greater than or equal to 1% by weight, preferably to less than or equal to 50% by weight, preferably greater than or equal to 3% by weight, greater than or equal to 5% by weight, greater than or equal to 7% by weight, of at least one plant extract selected from *Bid. alba, Bid. pilosa, Sta. jamaicensis, Sta. cayennensis, Sta. indica* and/or *Bur. simaruba, Bur. microphylla, Bur. glabrifolia*, based on the total content (T=100% by weight) of the tincture,
 at least one acidifier selected from acetic acid, citric acid, ascorbic acid, adipic acid, tartaric acid, mandelic acid and/or malic acid,
 greater than or equal to 1% by weight, preferably greater than or equal to 3 Gew.-%, greater than or equal to 5 Gew.-%, greater than or equal to 7 Gew.-%, greater than or equal to 10 Gew.-%, to each less than or equal to 70 Gew.-%, of a (d) *Aloe* extract, based on the total content of the tincture (T=100% by weight), and
 at least one excipient,
 wherein the tincture has a pH value greater than or equal to 3 to less than or equal to 9 and the tincture is an aqueous/ethanolic mixture, in particular a solution or dispersion, having an ethanol concentration greater than or equal to 70%, based on 100 ml total volume of the tincture (ad 100%). Preferably, the tincture described above comprises greater than or equal to 3% by weight, greater than or equal to 5% by weight, preferably greater than or equal to 7% by weight, total content of at least one plant extract according to the invention or combination from (a), (b) and/or (c), and preferably greater than or equal to 15% by weight of at least one (d) *Aloe* extract, respectively based on the total content the phyto-mixture (ad 100% by weight).

The tincture, solution, suspension, dispersion and semi-solid forms described above has preferred pH values, depending on its respective indication, which has been described in detail in connection with the acidifiers above.

Within the meaning of the invention, "aqueous/ethanolic mixture" comprises solutions and dispersions comprising insoluble ingredients and particles. Presence of the aqueous/ ethanolic mixture depends on solution behavior of the extracted ingredients, the separating step and depends on ethanol concentration.

The immunologically active phyto-mixture comprising at least one plant extract according to the invention from (a), (b), and/or (c), and, optionally, (d), preferably the composition comprising the phyto-mixture, for use in the prevention or in a method for treatment of efflorescences within the meaning of the invention, wherein the oral formulation (see Examples 8a-b and 9) is based on a solid form, is also preferred, wherein
- the solid form comprises at least one dry, in particular solvent-free, plant extract selected from *Bid. alba, Bid. pilosa, Sta. jamaicensis, Sta. cayennensis, Sta. indica, Bur. simaruba* and/or an *Aloe* species,
- the at least one plant extract is contained in a content of greater than or equal to 1% by weight, preferably greater than or equal to 3% by weight, greater than or equal to 5% by weight, greater than or equal to 7% by weight, based on the total content of the solid form (F=100% by weight),
- the residual moisture is less than or equal to 5% by weight, preferably less than or equal to 1% by weight and, particularly preferably, less than or equal to 0.1% by weight, based on the total content of the dry plant extract (F=100% by weight), and
- at least one excipient is contained.

Particularly preferred topical formulations are those for applying, depositing, massaging in, spraying on, dripping on and/or laying on the affected skin surface and thus for absorption of the immunologically active phyto-mixture through the skin or mucous membrane, in particular nasal and/or oral mucosa.

Particular preferred oral administration forms of the phyto-mixture according to the invention comprising at least one plant extract according to the invention (a), (b), and/or (c), and, optionally (d) comprise formulations for dissolving in a beverage and subsequent drinking, for swallowing (e.g. as tablet) and absorption trough the gastrointestinal tract, for oral intake and disaggregation in the oral cavity or depositing on the oral mucosa and absorption through the oral mucosa. Formulations for absorptions through the gastrointestinal tract preferably comprise no anthraquinones since they can have a laxative effect. Formulations according to the invention where laxative effect is desired preferably comprise no *Aloe* extract or anthraquinone-free *Aloe* extract. The same applies for the species according to the invention of genus (a) *Bidens*, (b) *Stachytarpheta* and (c) *Bursera*. The following examples elucidate the invention in more detail and only represent chosen embodiments, without limiting thereto. For this purpose, some species according to the invention were used as representatives of the respective genus (a) *Bidens*, (b) *Stachytarpheta* and (c) *Bursera* and for the species of the respective genus, described as being preferred.

EXAMPLES

Example 1: Source of the Used Plant Material

The plants *Bur. simaruba, St. jamaicensis, Bid. alba* and *Stem. maritima* disclosed and claimed within this patent application were respectively obtained from the Bahamas, Isle "Long Island", as representatives according to the invention of genus (a) *Bidens*, (b) *Stachytarpheta*, (c) *Bursera*, and (d) *Stemodia*. The Bahamian government issued appropriate certificates for harvest of the plants used herein and their export to Germany for research and experimental purposes ("Plant Protection Service of the Bahamas" Nr. 2928 and Nr. 2929 and "Permit to conduct Scientific Research in the Bahamas"). The experiments described subsequently were performed within the scope of this research permit and export authorization.

A: *Bidens alba* (*Bid. Alba*)/B: *Stachytarpheta jamaicensis* (*Sta. jamaicensis*)

Aboveground plant parts comprising stem, leaves, shoots and blossoms each were freshly harvested from young 1- to 3-years-old plants (A and B). These were dried at 40° C. to 55° C. for 6 to 20 hours and subsequently stored in a cool dry place.

Duration of drying and temperature is variably freely selectable according to the knowledge of the person skilled in the art.

C: *Bursera simaruba* (*Bur. Simaruba*)

Leaves and branches of a 5- to 20-years-old tree. The harvested leaves were dried at 57° C. to 62° C. for 8 to 20 hours and subsequently stored in a cool dry place.

D1: *Stemodia maritima* (*Stem. maritima*)

Aboveground approx. 1-year-old herb. The harvested herb was dried at 40° C. for 7 hours and subsequently stored in a cool dry place.

D2: *Aloe vera*

Starting material: 500 ml of an anthraquinone-free water extract of *Aloe vera* (allcura Naturheilmittel GmbH, Reichenäcker 7, 97877 Wertheim). 20 ml of the water extract were freeze-dried (Christ LMC-1, Delta 1-20 KD). Yield: dry weight 450 mg powder (about 22.5 mg/ml).

TABLE 1b

| | Plant material | | |
|---|---|---|---|
| Plant | Plant material as powder after crushing [g] | Dry weight water extract [g] | Dry weight ethanol extract [g] |
| A | 31.5 | 0.931 | 1.464 |
| B | 38.7 | 0.7275 | 2.485 |
| C | 33.1 | 1.1212 | 5.8 |
| D1 | 38.7 | 0.299 | 1.39 |
| D2 | ./. | 0.450 | ./. |

Example 2: Crushing of the Plant Material

The plant material described above with the described plant parts were provided, crushed and pulverized in a commercial blender for about 2 minutes. Subsequently, the respective powder was processed into, on the one hand, an aqueous and, on the other hand, an ethanolic extract.

Example 3: Production of an Aqueous Plant Extract

A *Bidens alba*—Aqueous Extract:

The powder was transferred into a three-necked flask with distilled water (8.2 g powder to 120 ml distilled water) and stirred at 40° C. for twice 4 hours each or 8 hours in all. A clear solution was obtained after subsequent filtration of the extract. The clear solution was freeze-dried for 64 hours (Christ LMC-1, Delta 1-20 KD). Yield after freeze-drying: 0.931 g B *Stachytarpheta jamaicensis*—Aqueous Extract:

8.0 g of the powder of *Stachytarpheta jamaicensis* were analogously processed to *Bidens alba*. Yield after freeze-drying: 0.7275 g C *Bursera simaruba*—Aqueous Extract:

8.2 g of the powder of *Bursera simaruba* were analogously processed to *Bidens alba*.

Yield after freeze-drying: 1.1212 g

D1 *Stemodia maritima*—Aqueous Extract:

8.1 g of the powder of *Stemodia maritima* were analogously processed to *Bidens alba*.

Yield after freeze-drying: 0.299 g

Example 4: Production of an Ethanolic Plant Extract

A *Bidens alba*—Ethanol Extract:

The powder (8.0 g) was filled into an extraction sleeve (Macherey & Nagel; MN 645; 23×100 mm) and extraction with reflux was performed using a Soxhlet extraction with 280 ml 96% ethanol at room temperature for 8 hours. The organic phase was filtrated through glass wool (company Migge No. 1408/3). Subsequently, the ethanol extract was evaporated until dryness using a Rotavapor (Heidolph; 50° C. water bath temperature, 112 bar). Yield: 1.464 g dry weight The dry weight was dissolved in 15 ml Ethanol in order to detach dry residues adhering to the bottom of the round-bottom flask. Subsequently, the solution was divided to sample containers for storing at −20° C. and dried by blowing through of nitrogen gas.

B *Stachytarpheta jamaicensis*—Ethanol Extract:

8.0 g of the powder of *Stachytarpheta jamaicensis* were analogously processed to *Bidens alba*. Yield: 2.485 g dry weight C *Bursera simaruba*—Ethanol Extract:

8.2 g of the powder of *Bursera simaruba* were analogously processed to *Bidens alba*.

Yield: 5.8 g dry weight

D1 *Stemodia maritima*—Ethanol Extract:

6.7 g of the powder of *Stemodia maritima* were analogously processed to *Bidens alba*.

Yield: 1.39 g dry weight

The residual content of ethanol of the above ethanol plant extracts was less than 0.1%.

Example 5: Determination of Cytotoxicity of the Produced Extracts

Cell Culture

HaCaT-Cells (human in vitro spontaneous transformed keratinocytes from histologically normal skin) of DMSZ (German Collection of Microorganisms and Cell Cultures) were kept in Dulbecco's modified Eagle Medium (DMEM) with glutamax (Invitrogen/Gibco, Karlsruhe, Germany) with 10% fetal calf serum (Sigma Aldrich, Germany), 100 U/ml penicillin and 100 µg/ml streptomycin and 1% NEAA.

The cells were cultivated at 37° C., 5% $CO_2$ and 95% humidity. The cells were subcultivated by removing the medium, adding 0.075% EDTA-solution in 1-fold PBS (phosphate-buffered salt solution) and subsequently incubated at 37° C. for 10 min. EDTA was removed und the HaCaT-cells were detached form the culture vessel by addition of 0.25% trypsin and 0.02% EDTA at 37° C. for 5 min. Afterwards, addition of fresh medium, centrifugation, exhausting of the medium and transferring in a new flask (ratio 1:5 or 1:10) was done. All experiments were performed using cells in the logarithmic growth phase.

Sample preparation: Aqueous extracts were dissolved in water (100 mg/ml water) and ethanol extracts in dimethylsulfoxide, DMSO, (200 mg/ml DMSO).

MTT-Assay According to Mosmann, 1983 (J. Of Immunological Methods 65, 55-63)

In order to determine the concentration dependent cytotoxicity $2 \times 10^4$ HaCaT-cells/sample well of a 96-well plate were transferred and incubated for 24 hours. Incubation of the HaCaT-cells was performed using 100 µl of the medium containing various concentrations of the respective plant extract (see Table 2) or a 1.1 mixture of two plant extracts (see Table 3). Subsequently, 0.5 mg/ml MTT (3-(4,5-Dimethylthiazole-2-yl)-2,5-diphenyltetrazoliumbromide) were added and incubated for 4 hours. After dissolving the formazan crystals formed by the HaCaT-cells in 100 µl DMSO (10 minutes shaking), absorption at 570 nm was measured (by means of Tecan Safire II Reader, Tecan Crailsheim, Germany). Doxorubicin was measured as reference. Cell vitality was determined according to the following formula:

$$\text{Vitality [\%]} = \frac{[(OD \text{ sample of untreated } HaCaT\text{-cells}) - (OD \text{ sample medium control})] * 100}{[(OD \text{ untreated } HaCaT\text{-cells}) - (OD \text{ medium control})]}$$

Statistical Analysis

Three-fold determination (n=3) with three-fold replicate was performed and the results were stated as means±standard deviation. $IC_{50}$-values were calculated through the dose response curve which was created by use of a logistic regression curve with 4 parameters with the GraphPad Prism® 5.01 Software or SigmaPlot® 11.0. The individual curves are not shown herein. The determined $IC_{50}$-values with standard deviations are summarized in Tables 2 and 3.

Results

None of the aqueous extracts *Bid. alba* (A-W), *Sta. jamaicensis* (B-W), *Bur. simaruba* (C-W), *Stem. maritima* and *Aloe vera* exhibits cytotoxicity compared to doxorubicin as cytotoxic reference compound (see Table 2).

Ethanolic plant extracts of *Bid. alba* and *Bur. simaruba* exhibit no cytotoxicity compared to doxorubicin as cytotoxic reference compound. Ethanolic extracts of *Sta. jamaicensis* and *Stem. maritima* exhibit low cytotoxicity.

Only the combinations with plant extracts of little higher $IC_{50}$-values were analysed again to cytotoxicity (see Table 3).

Example 6: Determination of Anti-Inflammatory Activity

Inhibition of 5-Lipoxygenase (5-LOX) through the individual extracts and their combinations (see Table 2 and 3) was spectroscopically determined (Baylac & Racine 2003). For this purpose 970 µl of the phosphate buffer (21.2 g K3PO4 in 1 L $H_2O$), pH 9.0 were mixed with 10 µl of 1 mg/ml concentrated 5-LOX (lyophilized powder, Fluka) and 20 µl various concentrations (0.48 µg/ml to 250 µg/ml) of the individual plant extracts and of the combinations (1:1 mixture). The mixture was incubated at room temperature for 10 minutes. Enzymatic reaction was initiated by adding of 20 µl of 5 mM sodium linoleate (Sigma Aldrich). Reaction kinetic was determined at 234 nm every 5 seconds by means of a WPA Biowave II spectrophotometer. Nordihydroguaiaretic acid (NDGA) was used as positive control of a 5-LOX-selective inhibitor.

Initial reaction speed was respectively determined from the slope of the linear part of the curve. Inhibition of the enzyme activity was calculated from three-fold experiments. Percentage of the initial activity was determined according to the following formula:

$$[\%] \text{ of the initial activity} = (IA_{control} - IA_{sample})/IA_{control} \times 100$$

wherein sample corresponds to an individual plant extract or a combination of at least two plant extracts and control equals to NDGA.

Percentage [%] of the initial activity was (y-axis) graphically plotted as a function of the concentration of the respective plant extract or the combination (1:1 mixture), in order to determine the $IC_{50}$-value as the concentration at which 50% of the enzyme activity is inhibited by the respective plant extract or the combination.

Results

Table 2 shows that ethanolic *Bur. simaruba* (C-E) extract exhibits significant inhibition of 5-Lipoxygenase. Consequently, an ethanol plant extract of *Bur. simaruba* (C-E withICso=132±13 µg/ml) exhibits provably significant anti-inflammatory activity. The same applies for the respective ethanol individual extracts of *Sta. jamaicensis* (B-E with $IC_{50}$=84±10 µg/ml) and *Bid. alba* (A-E with $IC_{50}$=139±7 µg/ml).

Table 3 shows that the combinations of the respective extracts exhibit an increased inhibition of 5-Lipoxygenase. These experiments respectively prove significant anti-inflammatory efficiency for *Bid. alba, Sta. jamaicensis* and *Bur. simaruba* as representatives for genus (a) *Bidens*, (b) *Stachytarpheta* and (c) *Bursera*. This efficiency may be attributed to the compounds, being contained in the species according to the invention and being extracted by means of the method according the invention, comprising verbascosides, flavonoids, iridoids, ipolamiides, fulvoipolamiides, sesquiterpene lactones and/or proazulenes.

TABLE 2

Individual extracts

| Extract | Plant | Cytotoxicity $IC_{50}$ [µg/ml] | 5-Lox-inhibition $IC_{50}$ [µg/ml] |
|---|---|---|---|
| A-W | *Bid. alba* | >3000 | >1000 |
| A-E | *Bid. alba* | 527 ± 68 | 139 ± 7 |
| B-W | *Sta. jamaicensis* | 1023 ± 153 | >1000 |
| B-E | *Sta. jamaicensis* | 546 ± 66 | 84 ± 10 |
| C-W | *Bur. simaruba* | 4670 ± 400 | >1000 |
| C-E | *Bur. simaruba* | 1800 ± 670 | 132 ± 13 |
| D1-W | *Stem. maritime* | 1399 ± 321 | >1000 |
| D1-E | *Stem. maritima* | 127 ± 5 | >1000 |
| D2 | *Aloe vera* | 3360 ± 860 | >1000 |
|  | Doxorubicin | 8.6 ± 2.03 | ./. |
|  | NDGA | ./. | 0.53 ± 0.09 |

W = aqueous extract;
E = ethanol extract, A, B, C, D1 and D2 corresponds to nomenclature from example 1.

TABLE 3

Extract combinations 1:1 mixture

| Extract combination 1:1 mixture | cytotoxicity $IC_{50}$ [µg/ml] | 5-Lox-inhibition $IC_{50}$ [µg/ml] |
|---|---|---|
| A-E/B-E | n.b. | 52 ± 1.3 |
| A-E/C-E | n.b. | 78 ± 6 |
| B-E/C-E | n.b. | 57 ± 8 |
| A-E/D1-E | 101 ± 15 | 98 ± 7.5 |
| B-E/D1-E | 117 ± 8.7 | 94 ± 4.5 |
| C-E/D1-E | 144 ± 16 | 99 ± 14 |
| A-E/D2 | n.b. | 115 ± 15 |
| B-E/D2 | n.b. | 73 ± 16 |
| C-E/D2 | 2710 ± 290 | 161 ± 23 |
| D1-E/D2 | 128 ± 13 | 130 ± 18 |
| Doxorubicin | 8.6 ± 2.03 | ./. |
| NDGA | ./. | 0.53 ± 0.09 |

W = aqueous extract;
E = ethanol extract, A, B, C, D1 and D2 corresponds to nomenclature from example 1.

Example 7: Determination of Antimicrobial Efficiency

Antibacterial efficiency of the respective plant extract as individual extract and as combination of two extracts was analysed against the following test germs:

Gram-Positive Bacteria

Methicillin resistant *Staphylococcus aureus* MRSA NCTC 10442 (MRSA NCTC 10442)

*Staphylococcus aureus* ATCC 25923 (*S. aureus* ATCC 25923)

*Staphylococcus epidermidis* ATCC 14990 (*S. epid.* ATCC 14990)

Gram-Negative Bacteria

*Pseudomonas aeruginosa* ATCC 27853 (*P. aerug.* ATCC 27853) and

*Acinetobacter baumanii* ATCC BAA747 (ATCC BAA747)

Culture Preparation

The bacteria were precultivated on Columbia medium with 5% sheep blood at 37° C. for 24 hours. On to two colonies were suspended in saline solution (0.9% NaCl) and adjusted to a turbidity of 0.5 McFarland standard which corresponds to $1\times10^8$ colony forming units per milliliter (CFU/ml). Subsequently, the suspension was diluted to $1\times10^6$ CFU/ml.

Determination of the Minimal Inhibitory Concentration (MIC) and the Minimum Bactericidal Concentration (MBC)

The MIC was determined by means of the microbouillon dilution process according to NCCLS (2006). For this purpose, the aqueous extracts were dissolved in water (w/v) and the ethanolic extracts in 5% DMSO (w/v) with 80 mg/ml each and Bur. simaruba as well as Aloe vera were suspended with 160 mg/ml. The extracts and the combinations (1:1 mixture) of two plant extracts were respectively transferred into a sample well of a 96-well plate. The individual extracts were respectively adjusted to a concentration of 4 mg/ml to 8 mg/ml and 0.03 mg/ml and the combinations to 2:2 mg/ml to 0.3:0.3 mg/ml. Subsequently, the bacteria suspensions with about $5\times10^5$ CFU/ml in Müller Hinton medium (Fluka) were respectively added. The accordingly fitted 96-well plates were incubated at 37° C. for 24 hours.

The MIC was determined at 600 nm on the basis of the turbidity. In order to determine the MBC, 3 µl of the suspension of the respective sample well were spread on an full culture medium and incubated at 37° C. for 24 hours. The MBC was determined as lowest concentrations of the respective extract which totally kills the microorganisms.

All experiments were performed as three-fold determination (Table 4 to 5). The antibiotics Vancomycin (briefly: Van) and Streptomycin (briefly: Strep) were used parallely to each experimental approach as positive control for antimicrobial efficiency (Table 5c). Respectively one of the mentioned test germs was carried along with the respectively solvent (water, DMSO) as negative control for an inhibiting effect by the used solvent. In comparison to the growth control without any addition, no negative influence on the growth was observed for all negative controls.

A sterility control confirmed sterility of the used media (data not shown). The composition of the controls is summarized in Table 5b.

Results

Table 4a summarizes the antimicrobial activity of the aqueous individual plant extracts. Table 4a shows antibacterial efficiency for Sta. jamaicensis (B-W) and Bid. alba (A-W). Stem. maritima (D1-W) exhibits higher antibacterial efficiency compared to B-W and A-W.

All the following combinations (1:1 mixture) of the aqueous extracts exhibit the same efficiency against gram-positive bacteria with MIC≥2/2 and MBC≥2/2:
A-W/B-W, A-W/C—W, B—W/C—W, C—W/D1-W, B—W/D1-W, A-W/D1-W, A-W/D2,
B-W/D2, C-W/D2, D1-W/D2

Table 5a summarizes the antimicrobial activity of the ethanolic extracts and Table 5b the combinations of the ethanolic plant extracts. The experiments clearly prove an antibacterial efficiency of Sta. jamaicensis and Bid. alba as well as of Stem. maritima. In particular, the afore-mentioned species exhibit significant efficiency against gram-positive bacteria and particularly against MRSA.

TABLE 4

Antimicrobial activity of the aqueous individual plant extracts

| Test germ | MIC C-W | MBC C-W | MIC B-W | MBC B-W | MIC A-W | MBC A-W | MIC D1-W | MBC D1-W | MIC D2 | MBC D2 | MIC Van | MBC Van | MIC Strep | MBC Strep |
|---|---|---|---|---|---|---|---|---|---|---|---|---|---|---|
| MRSA NCTC 10442 | >8 | >8 | 4 | >4 | >4 | >4 | 2 | 4 | 8 | >8 | 1 | 2 | ./. | n.b. |
| S. aureus ATCC 25923 | >8 | >8 | 4 | >4 | >4 | >4 | 2 | 4 | 4 | >8 | 0.5 | 0.5 | 2 | 8 |
| S. epid. ATCC 14990 | >8 | >8 | 4 | >4 | >4 | >4 | 2 | 4 | 8 | >8 | 1 | 2 | 1 | 8 |
| P. aerug. ATCC 27853 | >8 | >8 | >4 | >4 | >4 | >4 | >4 | >4 | >8 | >8 | ./. | n.b. | 4 | 8 |
| ATCC BAA747 | >8 | >8 | >4 | >4 | >4 | >4 | >4 | >4 | 8 | >8 | 64 | 128 | 2 | 4 |

TABLE 5a

Antimicrobial activity of the ethanolic individual plant extracts

| Test germ | MIC C-E | MBC C-E | MIC B-E | MBC B-E | MIC A-E | MBC A-E | MIC D1-E | MBC D1-E | MIC D2 | MBC D2 | MIC Van | MBC Van | MIC Strep | MBC Strep |
|---|---|---|---|---|---|---|---|---|---|---|---|---|---|---|
| MRSA NCTC 10442 | >8 | >8 | 2 | 4 | 4 | >4 | 0.5 | 1 | 8 | >8 | 1 | 2 | ./. | n.b. |
| S. aureus ATCC 25923 | >8 | >8 | 1 | 4 | 2 | 4 | 0.5 | 1 | 4 | >8 | 0.5 | 0.5 | 2 | 8 |
| S. epid. ATCC 14990 | >8 | >8 | 1 | 2 | 1 | 2 | 0.5 | 1 | 8 | >8 | 1 | 2 | 1 | 8 |
| P. aerug. ATCC 27853 | >8 | >8 | >4 | >4 | >4 | >4 | >4 | >4 | >8 | >8 | ./. | n.b. | 4 | 8 |
| ATCC BAA747 | 8 | >8 | 4 | >4 | 4 | >4 | 2 | 4 | 8 | >8 | 64 | 128 | 2 | 4 |

TABLE 5b

Antimicrobial activity of the ethanolic plant extracts combinations (1:1 mixture)

| Test germ | A-E/B-E MIC | A-E/B-E MBC | A-E/C-E MIC | A-E/C-E MBC | B-E/C-E MIC | B-E/C-E MBC | C-E/D1E MIC | C-E/D1E MBC | B-E/DQ-E MIC | B-E/DQ-E MBC | A-E/D1-E MIC | A-E/D1-E MBC |
|---|---|---|---|---|---|---|---|---|---|---|---|---|
| MRSA NCTC 10442 | 2/2 | >2/2 | >2/2 | 2>2/2 | 2/2 | >2/2 | 1/1 | 2/2 | 0.5/0.5 | 1/1 | 1/1 | 2/2 |
| S. aureus ATCC 25923 | 1/1 | >2/2 | 2/2 | >2/2 | 1/1 | >2/2 | 0.5/0.5 | 1/1 | 0.5/0.5 | 1/1 | 1/1 | 2/2 |
| S. epid. ATCC 14990 | 1/1 | 2/2 | 1/1 | >2/2 | 1/1 | 2/2 | 1/1 | 2/2 | 0.5/0.5 | 1/1 | 1/1 | 2/2 |

TABLE 5c

| Test germ | Positive controls (antimikro. effect) | | | |
|---|---|---|---|---|
| | MIC Van µg/ml | MBC | MIC Strep µg/ml | MBC |
| MRSA NCTC 10442 | 1 | 2 | ./. | n.b. |
| S. aureus ATCC 25923 | 0.5 | 0.5 | 2 | 8 |
| S. epid. ATCC 14990 | 1 | 2 | 1 | 8 |
| P. aerug. ATCC 27853 | ./. | n.b | 4 | 8 |
| ATCC BAA747 | 64 | 128 | 2 | 4 |

TABLE 5d

Composition of the controls

| | |
|---|---|
| Growth control | medium + test germ without extract/without antibiotic |
| Negative control | medium + test germ + solvent (water/DMSO) without extract/without antibiotic |
| Sterility control | medium without further additions |
| Positive control | medium + test germ + solvent (water/DMSO) + antibiotic (see Table 5c) |

| Name | Homeopathic trituration | Tea | Tablets & Pellets with and without film coating | Hard gelatin capsules | Soft gelatin capsules | Solution | Suspension | Semi-solid preparation | Powder | Filler | Accelerator for disaggregation, Disintegrant |
|---|---|---|---|---|---|---|---|---|---|---|---|
| 1,2-Propylene glycol | 1 | | 1 | 1 | 1 | 1 | | | | | |
| Acetyltributylcitrate | | | 1 | 1 | 1 | | | | | | |
| Agar agar | | | | | | | | | | | 1 |
| Alkyl-4-hydroxybenzoate | | | | 1 | 1 | 1 | 1 | | | | |
| Aluminium-fatty acid compounds | | | 1 | 1 | 1 | | | | 1 | | |
| Aluminium oxide/hydroxide | | | 1 | 1 | | | | | 1 | 1 | |
| Gum arabic | | | 1 | 1 | 1 | | | | 1 | 1 | |
| Essential oils | | 1 | | 1 | 1 | 1 | 1 | 1 | | | |
| Benfonife | | | | 1 | 1 | 1 | 1 | 1 | | | |
| Calcium carbonate | | | 1 | 1 | | | | | 1 | 1 | |
| Calcium hydrogenphosphate | 1 | | 1 | 1 | | | | 1 | 1 | 1 | |
| Carboxymethylcellulose sodium | | | 1 | 1 | | 1 | 1 | 1 | | | 1 |
| Carotine | | | 1 | 1 | 1 | | | | | | |
| Cellulose | | | 1 | 1 | | 1 | 1 | | | 1 | |
| Cellulose acetate phthalate | | | 1 | 1 | | | | | | | |
| Cetylalcohol | | | 1 | 1 | 1 | 1 | 1 | 1 | | | |
| Cetylstearylalcohol | | | 1 | | 1 | | | 1 | | | |
| Citric acid | | | 1 | 1 | 1 | 1 | 1 | | | | |
| Dextrose | | | 1 | 1 | | | | | 1 | 1 | |
| Dibutyl/Diethylphthalate | | | 1 | 1 | 1 | | | | | | |
| Dimethylpolysiloxane | | | | 1 | 1 | | 1 | 1 | | | |
| Iron oxide | | | 1 | 1 | 1 | | | | | | |
| Ethylalcohol | 1 | | | 1 | 1 | 1 | 1 | | | | |
| Ethylcellulose | | | 1 | 1 | | | | | | | |
| Gelatine | | | 1 | 1 | 1 | 1 | 1 | | | | |
| Glycerol triacetate | | | 1 | 1 | 1 | | | | | | |
| Glycine | 1 | | | 1 | 1 | 1 | | | 1 | 1 | |
| Glycerol | 1 | | 1 | 1 | 1 | 1 | 1 | 1 | | | |
| Glycerol monostearate | | | 1 | 1 | 1 | | | 1 | | | |
| highly dispersed silicon dioxide | 1 | | 1 | 1 | 1 | 1 | 1 | | 1 | | |
| Hydroxypropylmethylcellulose (HPMC) | | | 1 | 1 | | 1 | 1 | | | | |
| Hydroxypropylmethylcellulose phthalate | | | 1 | 1 | | | | | | | |
| Isopropylalcohol | 1 | | | | | 1 | | 1 | | | |
| Isopropylmyristate | | | | 1 | 1 | | | 1 | | | |
| Lactose | 1 | | 1 | 1 | | | | | 1 | 1 | |
| Lecithin | | | | | 1 | | | 1 | | | |
| Macrogol 1000-glycerol monolaurate, -monostearate, -monooleate | | | | | | | | 1 | 1 | | |
| Macrogol 1500-glycerol triricinoleate | | | | | | | | 1 | | | |
| Macrogol glycerol hydroxystearate | | | | | | | | 1 | | | |

-continued

| Ingredient | | | | | | | | | | | | | |
|---|---|---|---|---|---|---|---|---|---|---|---|---|---|
| Macrogol stearate 400 | | | | | | | | | | | 1 | | |
| Magnesium stearate | | | | | | | | | | | | | |
| Maltodextrin | 1 | | | 1 | | | | | | | | | |
| Mannitol | | 1 | | 1 | | | | | | | | | |
| Methylcellulose | | | | 1 | | | 1 | | | | | | |
| Sodium cetylstearylsulfate | | | | 1 | | | 1 | | | | | | |
| Sodium dioctylsulfosuccinate (also K salts, Ca salts) | | | | 1 | 1 | | 1 | | | | | | |
| Sodium dodecylsulfate | | | | 1 | 1 | | 1 | | | | | | |
| Sodium hydrogencarbonate | | | | | 1 | | 1 | | | | | | |
| Oleic acid-oleylester | | | | | | | 1 | | | | | | |
| Pectin | | | | | | | 1 | | | | | | |
| Poloxamer | | | | 1 | | | 1 | | | | | | |
| Polyacrylic acid | | | | | | | 1 | | | | | | |
| Polyethylene glycol | | | | 1 | 1 | | 1 | | | | | | |
| Polyethylene oxide | | | | 1 | 1 | | 1 | | | | | | |
| Polymethacrylate | | | | 1 | | | 1 | | | | | | |
| Polyoxyl 23 laurylether, -20 cetostearylether, -10 oleylether | | | | | 1 | | | | | | | | |
| Polyoxyl 40 stearate, -50 stearate | | | | | 1 | | | | | | | | |
| Polysorbate 20, 60, 80, 40 | | | | | 1 | | 1 | | | | | | |
| Polyvinylacetate copolymers | | | | | 1 | | | | | | | | |
| Polyvinylalcohol | | | | | 1 | | 1 | | | | | | |
| Polyvinylpyrrolidone | | | | | 1 | | 1 | | | | | | |
| Riboflavin | | | | | | | | | | | | | 1 |
| Castor oil | | | | | | | 1 | | | | | | |
| Sucrose | | | | 1 | | | | | | | | | |
| Sorbitan monooleate, -palmitate, -stearate, -trioleate, -tristearate, -laurate | | | | 1 | | | 1 | | | | | | |
| Sorbitol | | | | 1 | | | | | | | | | |
| Starch | | | | 1 | | | | | | | | | |
| Starches, rice-, maize-potato-, wheat- | | | | 1 | | | | | | 1 | | | |
| Stearic acid | | | | 1 | | | 1 | | | 1 | | | |
| Stearylalcohol | | | | | | | 1 | | | 1 | | | |
| Talcum | | | | 1 | | | 1 | | | 1 | | | |
| Titanium dioxide | | | | | | | 1 | | | | | | |
| Tragacanth | | | | | | | | | 1 | | | | |
| Triacetin | | | | | | | | | | | | | |
| Triethanol amine | | | | 1 | | | | | | | | | |
| Triethylcitrate | | | | | | | 1 | | | | | | |
| Tromethamol | | | | | | | | | | | | | |
| Vaseline | | | | 1 | | | | | | | | | |
| Tartaric acid | | | | | | | 1 | | | | | | |
| Urea (Urea) | | | | | | | | | | | | | 1 |
| Ceramides | | | | | | | | | | | | | 1 |
| Hyaluronic acid | | | | | | | | | | | | | 1 |

TABLE -continued

| Name | Lubricant, Grease, Release agent, Glidant | Solvent, Solution accelerator | Emulsifier, Solubilizing agent, Solubilizer, Wetting agent, Antifoam agent | Salt forming agent, Buffer | Gel forming agent, Thickening agent, Film forming agent | Sorbent (Humectant- or Desiccant, respectively) | Sweetener | Colorant | Plasticizer | Basis e.g. for powder, Matrix forming agent | Stabilizer |
|---|---|---|---|---|---|---|---|---|---|---|---|
| 1,2-Propylene glycol | | | | | | | | | 1 | | |
| Acetyltributylcitrate | | | | | | | | | 1 | | |
| Agar agar | | | | | | | | | | | 1 |
| Alkyl-4-hydroxybenzoate | | | | | | | | | | | 1 |
| Aluminium-fatty acid compounds | | | | | | | | | | | |
| Aluminium oxide/hydroxide | | | | | | 1 | | | | | |
| Gum arabic | | | | | 1 | | | | | | |
| Essential oils | | | | | | | | | | | |
| Benfonife | | | | | 1 | | | | | | |
| Calcium carbonate | | | | 1 | | | | | | | |
| Calcium hydrogenphosphate | | | | | 1 | | | | | | |
| Carboxymethylcellulose sodium | | | | | 1 | | | | | | |
| Carotine | | | | | | | | 1 | | | |
| Cellulose | | | | | 1 | 1 | | | | | 1 |
| Cellulose acetate phthalate | | | | | | | | | | | |
| Cetylalcohol | | | 1 | | | | | | | | |
| Cetylstearylalcohol | | | 1 | | | | | | | | |
| Citric acid | | | | 1 | | | | | | | |
| Dextrose | | | | | | | 1 | | | | |
| Dibutyl/Diethylphthalate | | | | | | | | | 1 | | |
| Dimethylpolysiloxane | 1 | | | | | | | | | | |
| Iron oxide | | | | | | | | 1 | | | |
| Ethylalcohol | | 1 | | | | | | | | | |
| Ethylcellulose | | | | | 1 | | | | | | |
| Gelatine | | | | | 1 | | | | | 1 | |
| Glycerol triacetate | | | | | 1 | | | | 1 | | |
| Glycine | | | | 1 | | | | | | | |
| Glycerol | | 1 | | | | 1 | | | 1 | | |
| Glycerol monostearate | | | 1 | | | | | | | | |
| highly dispersed silicon dioxide | 1 | | | | | | | | | | |
| Hydroxypropylmethylcellulose (HPMC) | | | | | 1 | | | | | 1 | |
| Hydroxypropylmethylcellulose phthalate | | | | | 1 | | | | | 1 | |
| Isopropylalcohol | | 1 | | | | | | | | | |
| Isopropylmyristate | | 1 | 1 | | | | | | | | |
| Lactose | | | | | | | | | | | |
| Lecithin | | | 1 | | | | | | | | |
| Macrogol 1000-glycerol monolaurate, -monostearate, -monooleate | | | | | | | | | | | 1 |

-continued

| Ingredient | | | | | | | | | | |
|---|---|---|---|---|---|---|---|---|---|---|
| Macrogol 1500-glycerol triricinoleate | | | | | | | | | | 1 |
| Macrogol glycerol hydroxystearate | 1 | | | | | | | | | |
| Macrogol stearate 400 | 1 | | | | | | | | | |
| Magnesium stearate | 1 | | | | | | | | | |
| Maltodextrin | | | | | | | | | | 1 |
| Mannitol | | | 1 | | | | | | | |
| Methylcellulose | 1 | | 1 | | | | | | | |
| Sodium cetylstearylsulfate | 1 | | | | | | | | | |
| Sodium dioctylsulfosuccinate (also K salts, Ca salts) | 1 | | | | | | | | | |
| Sodium dodecylsulfate | 1 | | | | | | | | | |
| Sodium hydrogencarbonate | | 1 | | | | | | | | |
| Oleic acid-oleylester | | | | 1 | | | | | | |
| Pectin | | | | 1 | | | | | | |
| Poloxamer | 1 | | | | | | | | | |
| Polyacrylic acid | | | | 1 | | | | | | |
| Polyethylene glycol | 1 | | | 1 | | 1 | | | | |
| Polyethylene oxide | 1 | | | 1 | | 1 | | | | |
| Polymethacrylate | 1 | | | 1 | | | | | | |
| Polyoxyl 23 laurylether, -20 cetostearylether, -10 oleylether | 1 | | | | | | | | | |
| Polyoxyl 40 stearate, -50 stearate | 1 | | | 1 | | | | | | |
| Polysorbate 20, 60, 80, 40 | | | | 1 | | | | | | |
| Polyvinylacetate copolymers | | | | 1 | | | | | | |
| Polyvinylalcohol | | | | 1 | | | | | | |
| Polyvinylpyrrolidone | 1 | | | | | 1 | | | | |
| Riboflavin | | | | | | | 1 | | | |
| Castor oil | | | | 1 | | | | | | |
| Sucrose | | | | 1 | 1 | | | | | |
| Sorbitan monooleate, -palmitate, -stearate, -trioleate, -tristearate, -laurate | 1 | | | | | | | | | |
| Sorbitol | 1 | | | 1 | 1 | | | | | |
| Starch | 1 | | | | | | | | | |
| Starches, rice-, maize-potato-, wheat- | | | | 1 | | | | | | |
| Stearic acid | 1 | | | | | 1 | | | | |
| Stearylalcohol | 1 | | | | | | | | | |
| Talcum | 1 | | | | | | | | | |
| Titanium dioxide | | | 1 | | | | | | | |
| Tragacanth | | | | 1 | | | | | | |
| Triacetin | | | | 1 | | 1 | | | | |
| Triethanol amine | | | | | | 1 | | | | |
| Triethylcitrate | 1 | | | | | 1 | | | | |
| Tromethamol | 1 | | | | | | | | | |
| Vaseline | | | | | | | 1 | | | |
| Tartaric acid | | | | 1 | | | | | | |
| Urea (Urea) | | | | 1 | | | | | | |
| Ceramides | | | | | | | 1 | | | |
| Hyaluronic acid | | | | 1 | | | | | | |

For example, the excipients ethyl- and methylcellulose, hydroxypropylmethylcellulose, cellulose acetate phthalate and hydroxypropylmethylcellulose phthalate exhibit retarding properties.

Example 8b Formulas

Base Formula: Moisturizing Cream
100 g base cream DAC comprises:
4.0 g glycerol monostearate 60
6.0 g cetylalcohol
7.5 g medium chain triglycerides (neutral oil, Miglyol 812)
25.5 g white vaseline Base Tincture D2a (Total: 100% by Weight Based on the Dry Weight):

70% by weight of an *Aloe* extract (D2) were homogenously mixed in 100 ml 90% ethanol Base Tincture D2b (Total: 100% by Weight Based on the Dry Weight):

30% by weight of an *Aloe* extract (D2) were homogenously mixed in 100 ml 90% ethanol 4. Immunologically Active Tinctures with A-E, B-E, C-E and D2

100 ml base tincture D2a or D2b were respectively mixed with:

TABLE 6

| | Mixture | | | | | | | | | |
|---|---|---|---|---|---|---|---|---|---|---|
| Plant extract | 44 (1:1:1) | 45 (1:1) | 46 (1:1) | 47 (1:1) | 48 (1:1:1) | 49 (1:1:1) | 50 (1:1:1) | 51 (1:1:3) | 52 (3:1) | 53 (1:3:1) |
| | | | | | % by weight | | | | | |
| Bid. alba (A-E) | 1 | 1.5 | 1.5 | 2.5 | 2 | 5 | 7 | 0.5 | 0 | 0.5/5 |
| Sta. jamaicen. (B-E) | 1 | 0 | 1.5 | 0 | 2 | 5 | 7 | 0.5 | 1.5/15 | 1.5/15 |
| Bur. simaruba (C-E) | 1 | 1.5 | 0 | 2.5 | 2 | 5 | 7 | 1.5 | 0.5/5 | 0.5/5 |

7.0 g Macrogol 20-glycerol monostearate
10.0 g propylene glycol
40.0 g purified water
1. Formula: Moisturizing Cream with C-E. B-E and D2
40 to 97 g of the base formula
1-10 g *Bursera simaruba* (C-E)
1-10 g *Stachytarpheta jamaicensis* (B-E)
1-40 g *Aloe vera* (D2)
(total weight 100 g=100% by weight, each based on the dry weight)
2. Formula: Moisturizing Cream with B-E. A-E and D2
40 to 97 g of the base formula
1-10 g *Stachytarpheta jamaicensis* (B-E)
1-10 g *Bidens alba* (A-E)
1-40 g *Aloe vera* (D2)
(total weight 100 g=100% by weight, each based on the dry weight)
3. Formula: Moisturizing Cream with A-E, B-E, C-E and D2
30 to 96 g of the base formula
1-10 g *Bursera simaruba* (C-E)
1-10 g *Stachytarpheta jamaicensis* (B-E)
1-10 g *Bidens alba* (A-E)
1-40 g *Aloe vera* (D2)
(total weight 100 g=100% by weight, each based on the dry weight)

The % by weight information in Table 6 is based on the dry weight of the extracts obtained according to Example 3 or 4, preferably according to Example 4.

Depending on the desired indication of the skin, the pH value of the afore-mentioned tinctures 44 to 53 was set to:
(a) tincture for the skin: pH 4.5 to 5.5
(b) tincture for the oral mucosa: pH 6.7 to 7.2
(c) tincture for the eye: pH 7.0 to 7.5
(d) tincture for the nasal mucosa: pH 5.5 to 6.5
(e) tincture for ears: pH 5.5 to 6.1

The afore-mentioned mixtures and % by weight ratios (Table 6) may vary depending on the indication. For example, in the case where strengthened antimicrobial effect is desired, e.g. in the case of bacterial infections of the (mucous membrane) skin or in the mouth (gums), it is advantageous according to the invention to combine the extracts (or dry extracts) having the strongest antimicrobial effects (Table 5a/5b), or to use only one extract, e.g. A-E, (e.g. mixture 52 or 53). In contrast, in the case of strong inflammation, e.g. eye or ear, it may advantageous according to the invention to increase the content of particularly anti-inflammatorily effective extracts, e.g. A-E and/or C-E (Table 2 and 3). In this case, e.g. mixture 45 or mixture 45 having increased % by weight of each 5-20% by weight of the respective dry extract would be conceivable. In the case of antimicrobial ant anti-inflammatory indication at the same time, the appropriate combination according to the invention is to be chosen depending on the therapeutic goal.

Example 9: Application on the Skin

| Patient (f/m) | Symptom disease | Phyto-mixture | Dosage | Application | Course |
|---|---|---|---|---|---|
| 4 (f) | Lymphedema (re or li), upper arm partially forearm approx. 2 cm more in diameter | B + C + mint (flavor) | 5 cups per day fresh, strong, very green, | Tea, warm, internal | 5 to 6 hours under observation, after 2 to 3 hours symptomatical improvement after two days: regression, tension reduction, no lymphedema anymore |
| 2b (m) | Dry skin, pruritus, scratch marks, urticarial eczema, left, i.p, forearm, crook of the arm. | A + B + C + D2 (base tincture D2a + 44) | Of approx. 200 mg in 5 days maximally 50 ml used, coarse | Tincture approx. 1-4/day applied, 2 days → still × 3 day. Afterwards, partially gently creamed (dry skin). | On the same day relief. After 2 days only still scratch marks (crusts) left, but dry skin. From 5. day still tiny remains scratch marks, but dry skin. |
| 1d | Oral herpes, area approx. 6 × 4 mm, after 3-4 hours already big swelling, blister | A + B + C + D2 (base tincture D2a + 51) | Dropwise 3-4/day | Tincture dropwise 3-4/day applied on the oral herpes | First, no expansion anymore, then fast easing of the symptoms and of the swelling; desiccation within 2 days; no inflammation anymore; small crust which healed after some days through humid wound care with tincture and zinc ointment ⇒Aciclovir ointment functioned worse |
| 1e | Verrucous papillomas at 3 areas, 5-12 mm big, dermatologically removed by Erygenum laser; after 2 days all 3 inflamed; day 3: plaster change and spraying on of skin disinfection; day 4: inflammation increased; purulent secretion formation | A + B + C + D2 (base tincture D2a + 51) | Dropwise 1-2/day | Dropwise approx. 1-2/day, from day 5 the affected area thoroughly wetted with tincture | Day 5: Starting treatment because of inflammation and adhesion to the plaster, commencing secretion on day 5; the inflammatory pains eased quickly. On day 2 of the application first crust formation, little secretion; sometimes light itching; day 3 of the application: no secretion anymore ⇒fast healing, inflammation quickly away |
| 18.1 | 4-5 inflammatory insect bites, 5-8 mm big; dark reddening, swelling, itching, painful; partially | A + B + C + D2 (base tincture D2a + 51) | Dropwise several times/day | Insect bites wetted with the tincture several times a day | Itching eased quickly; within a few hours to one day no inflammation anymore; only |

-continued

| Patient (f/m) | Symptom disease | Phyto-mixture | Dosage | Application | Course |
|---|---|---|---|---|---|
| | secretion and scratch marks | | | | small areas without swelling visible; on day 2 of the application totally healed |
| 19 (f) | 38-year old with breast cancer; not familially predisposed; tendency to inflamed breast; i.a. skin problems, breast reddened, hardened, painful, inflammatory | A + B + C + D2 (base tincture D2a + 51) in combination with a tea with Bursera simaruba (C) | 2-3/day as application | A cloth was soaked with the tincture; cloth laid onto the breast as application with 30-60 min exposure time | Daily improved condition, inflammation and pains eased quickly After 1.5 years after completion of treatment no recurrence of the breast inflammations etc.; breast cancer was removed (Course not known) |

What is claimed is:

1. A method for treating eczema, acne, or psoriasis in a human or animal in need thereof, the method consisting essentially of administering to the human or animal in need thereof a therapeutically effective amount of a mixture consisting essentially of:
 a first ethanolic extract from a plant selected from the group consisting of (a) *Bidens alba* and *Bidens pilosa*, and combinations thereof; and
 a second ethanolic extract from a plant selected from the group consisting of (b) *Stachytarpheta jamaicensis, Stachytarpheta cayennensis, Stachytarpheta indica* and combinations thereof
 to effectively treat the eczema, acne, or psoriasis in the human or animal in need thereof.

2. The method of claim 1, wherein the mixture further consists essentially of at least one additional extract of a biologically active plant selected from the group consisting of *Bursera simaruba, Bursera microphylla, Bursera glabrifolia, Aloe, Stemodia maritima* and combinations thereof.

3. The method of claim 1, wherein the mixture has a pH of greater than or equal to 3.5 to less than or equal to 7.8.

4. The method of claim 1, wherein the mixture exhibits antibacterial activity against a transient skin flora selected from the group consisting of *Staphylococcus* sp., *Streptococcus* sp., methicillin-resistant *Staphylococcus aureus*, a Pseudomonad, and an *Acinetobacterium*, and any combination thereof.

5. The method of claim 1, wherein the eczema, acne, or psoriasis affects a site of the human or animal in need thereof selected from the group consisting of the skin of the limbs, the skin of the extremities, the skin of the joints, the skin of the head, the skin of the upper head, the skin of the outer ear, the skin of the nose, the nasal mucosa, the lips, the oral mucosa, the skin of the eye, the cornea, the conjunctiva, and the mucous membrane of the eye.

6. The method of claim 1, wherein the mixture exhibits antibacterial activity at a concentration of greater than or equal to 10 µg/ml to less than or equal to 10 mg/ml measured as minimal inhibitory concentration and/or as minimum bactericidal concentration.

7. The method of claim 1, wherein the mixture exhibits anti-inflammatory activity at a concentration of less than or equal to 200±10 µg/ml measured as $IC_{50}$ of 5-LOX inhibition.

8. The method of claim 1, wherein the mixture consists essentially of at least one compound selected from the group consisting of a flavonoid, a verbascoside, a phenylethanoid glycoside, a phenylpropanoid glycoside, a saponin, an iridoid, an ipolamiide, an iridoide-ipolamiide, an acteoside, a fulvoipolamiide, a phenolic acid, a polyphenol, a polysaccharide, a glycosylate, a terpene, a monoterpene, a sesquiterpene lactone, a anthrachchinone, a proazulene, a sulfide, a carotenoid, a vitamin A, a vitamin B, a vitamin C, a vitamin D, a vitamin E, an amino acid, and a mineral.

9. The method of claim 1, wherein the mixture is present in a form selected from the group consisting of a solution, a dispersion, a suspension, an emulsion, a tincture, a syrup, a juice, a tea, a tablet, a powder, a dragee, a globule, a granule, a lyophilisate, and a capsule, an aerosol, a spray, an emulsion, a lotion, and a cream.

10. The method of claim 1, wherein the mixture is in a liquid form and has a pH tolerated by the skin of the human or animal of greater than or equal to 3 and less than or equal to 9, a pH tolerated by the oral mucosa of greater than or equal to 6 and less than or equal to 8, a pH tolerated by the nasal mucosa of greater than or equal to 5 and less than or equal to 7, or a pH tolerated by the eye of greater than or equal to 7 and less than or equal to 9.

11. The method of claim 1, wherein the mixture is formulated for oral administration or topical administration to a region of the skin on the human or animal, and further wherein the immunologically active phyto-mixture is formulated as a form selected from the group consisting of a tablet, a powder, a granule, an effervescent tablet, a dry syrup, a dragee, a globule, a capsule, a lyophilisate, a suspension, a solution, a dispersion, a tincture, a concentrate, a tea, spray or an aerosol, a powder, a bath additive, a hip bath powder; an emulsion, a dispersion, a lotion, a cream, an ointment, and a paste.

12. The method of claim 1, wherein the mixture is formulated as a tincture which consists essentially of greater than or equal to 1% by weight based on the total weight of the tincture of at least one ethanolic plant extract selected from the group consisting of (a) an ethanolic plant extract from *Bidens alba* and an ethanolic plant extract from *Bidens pilosa*, and further consists essentially of one further ethanolic plant extract selected from the group consisting of (b) an ethanolic plant extract from *Stachytarpheta jamaicensis, Stachytarpheta cayennensis*, and *Stachytarpheta indica*, and further consisting essentially of an extract selected from the group consisting of (c) an ethanolic plant extract from *Bursera simaruba, Bursera microphylla, Bursera glabrifolia* and *Aloe*; at least one acidifier selected from the group consisting of acetic acid, citric acid, ascorbic acid, adipic acid, tartaric acid, mandelic acid, and malic acid; and greater than or equal to 1% by weight based on the total weight of the tincture of an *Aloe* extract, based on the total weight of the tincture, and further wherein the tincture has a pH value of greater than or equal to 3 to and less than or equal to 9 and is an aqueous/ethanolic mixture having an ethanol concentration greater than or equal to 70%, based on the total volume of the tincture.

13. The method of claim 1, wherein the mixture is formulated as an oral formulation in a solid form, and further wherein the solid form consists essentially of at least one dried ethanolic plant extract from a plant selected from the group consisting of *Bid. alba* and *Bid. pilosa*, and at least one further dried ethanolic plant extract from a plant selected from the group consisting of *Stachytarpheta jamaicensis, Stachytarpheta cayennensis, Stachytarpheta indica*, and one further ethanolic plant extract selected from *Aloe* and/or *Bursera simaruba*; wherein the at least one plant extract is present in a content of greater than or equal to 1% by weight of the total weight of the solid form, and the residual moisture in the solid form is less than or equal to 5% by weight of the dry plant extract.

14. The method of claim 1, wherein the mixture is formulated as a medicament, medical product, nutritional supplement, cosmetic, or is formulated as an immunologically active additive.

15. The method of claim 1, wherein the human or animal in need thereof is a human.

16. A method for producing the mixture of claim 1, the method consisting essentially of:
providing at least one above and/or underground plant part of at least one first plant selected from (a) and at least one second plant selected from (b), and at least one further plant selected from (c) *Bursera simaruba, Bursera microphylla, Bursera glabrifolia* or (d) *Aloe;*
extracting each plant part with 70-100% aqueous ethanol;
obtaining an ethanolic extract from each plant part; and
mixing at least two of the ethanolic extracts obtained, one being selected from (a) and at least one other being selected from (b), and further extracting from a plant selected from (c) or (d) *Aloe*, to produce a first ethanolic extract mixture,
whereby an immunologically active phyto-mixture is produced.

17. The method of claim 16, wherein the at least two plant extracts are obtained in liquid form, in dry form, or as mixture of solid and liquid forms.

18. The method of claim 16, further consisting essentially of performing a further processing step, wherein the further processing step is selected from the group consisting of drying, crushing, grinding using a mill, processing in a mortar, and dispersing the ethanolic extract, and combinations thereof.

19. The method of claim 16, further consisting essentially of adding an additional extract from a plant selected from the group consisting of (b), (c), (d), and combinations thereof to the mixture to produce a second mixture.

* * * * *